US006245937B1

(12) United States Patent
Cheng et al.

(10) Patent No.: US 6,245,937 B1
(45) Date of Patent: Jun. 12, 2001

(54) LIQUID PHASE PARALLEL SYNTHESIS OF CHEMICAL LIBRARIES

(75) Inventors: Soan Cheng; John Saunders, both of San Diego, CA (US)

(73) Assignee: DuPont Pharmaceuticals Research Laboratories, Inc., San Diego, CA (US)

( * ) Notice: Subject to any disclaimer, the term of this patent is extended or adjusted under 35 U.S.C. 154(b) by 0 days.

(21) Appl. No.: 08/959,495

(22) Filed: Oct. 28, 1997

Related U.S. Application Data

(60) Provisional application No. 60/029,506, filed on Nov. 29, 1996.

(51) Int. Cl.[7] ...................... C07C 229/00; C07C 233/00; G01N 33/53; G01N 33/566

(52) U.S. Cl. ................. 562/433; 435/6; 435/7.1; 435/DIG. 34; 436/501; 436/518; 436/536; 530/334; 544/386; 561/561; 564/152; 564/157

(58) Field of Search ................. 435/7.1, 6; 436/501, 436/518, 536; 562/869, 433; 530/334; 544/386; 564/152, 167

(56) References Cited

U.S. PATENT DOCUMENTS 5,840,485 * 11/1998 Lebl et al. ........................ 435/6

FOREIGN PATENT DOCUMENTS

WO 94/03483 * 2/1994 (WO) ....................... C07K/5/08

OTHER PUBLICATIONS

Greene and Wuts. Protective Groups in Organic Synthesis, 2nd ed., pp. 309–397, 1991.*
Cheng et al. "Novel Solution Phase Strategy . . ." J. Am. Chem. Soc., vol. 118, pp. 2567–2573, Mar. 1996.*
Cathala et al. "Macrobicyclic and Macrotricyclic Tetralactams . . ." Tet. Lett., vol. 35, No. 12, pp. 18633–1866. 1994.*
Anderson et al., "Analytical Techniques in Combinatorial Chemistry: MAS CH Correlation in Solvent–Swollen Resin", *J. Org. Chem.*, 60:2650 (1995).
Backes et al., "Carbon—Carbon Bond–Forming Methods on Solid Support. Utilization of Kenner's 'Safety–Catch' Linker" *J. Am. Chem. Soc.*, 116:11171–11172 (1994).
Bayer et al., "Kinetic Studies of the Liquid Phase Peptide Synthesis", *J. Am. Chem. Soc.*, 96(23):7333–7336 (1974).
Bayer et al., "Liquid Phase Synthesis of Peptides", *Nature* 237:512–513 (1972).
Bayer et al., "Automatically Programmed Synthesizer For the Liquid Phase Synthesis", *PEPTIDES: Chemistry, Structure and Biology*, Proceedings of the Fourth Annual Peptide Symposium 425–432 (1975).
Berger et al. "An Antidiabetic Thiazolidinedione Potentiates Insulin Stimulation of Glycogen Synthase in Rat Adipose Tissue", *Endocrinology* 137(5):1984–1990 (1996).

Bonora et al., "PEG–Supported Synthesis of Cyclic Oligodeoxyribonucleotides", *Nucleosides and Nucleotides*, 12:21–23 (1993).
Bonora et al., "HELP (High Efficiency Liquid Phase) New Oligonucleotide Synthesis on Soluble Polymeric Support", *Nucleic Acids Res.*, 8(11):3155–3159 (1990).
Bonora et al., "Large–Scale, Peg–Supported DNA Synthesis", *Nucleosides and Nucleotides*, 10(1–3):269–273 (1991).
Brummel et al.,, "A Mass Spectrometric Solution to the Address Problem of Combinatorial Libraries", *Science* 264:399–401 (Apr. 15, 1994).
Bunin et al., "A General and Expedient Method for the Solid–Phase Synthesis of 1,4–Benzodiazepine Derivatives", *J. Am. Chem. Soc.*, 114:10997–10998 (1992).
Chen et al., "'Analogous' Organic Synthesis of Small–Compound Libraries: Validation of Combinatorial Chemistry in Small–Molecule Synthesis", *J. Am. Chem. Soc.* 116:2661–2662 (1994).
Cheng et al., "Design and Synthesis of Novel Cyclic RGD–Containing Peptides as Highly Potent and Selective Integrin $\alpha_{IIb}\beta_3$ Antagonists", *J. Med. Chem.* 37(1):1–8 (Jan. 7, 1994).
Chu et al., "Free Solution Identification of Candidate Peptides from Combinatorial Libraries by Affinity Capillary Electrophoresis/Mass Spectrometry", *J. Am. Chem. Soc.*, 117:5419–5420 (1995).
Clark–Lewis et al., "Structure–Activity Relationships of Interleukin–8 Determined Using Chemically Synthesized Analogs", *J. Biol. Chem.* 266(34):23128–23134 (1991).
Egner et al., "Solid Phase Chemistry: Direct Monitoring by Matrix–Assisted Laser Desorption/Ionization Time of Flight Mass Spectrometry. A Tool for Combinatorial Chemistry",*J. Org. Chem.* 60:2652–2653 (1995).
Fitch et al., "High–Resolution $^1$H NMR in Solid–Phase Organic Synthesis", *J. Org. Chem.* 59:7955–7956 (1994).
Gallop et al., "Applications of Combinatorial Technologies to Drug Discovery. 2. Combinatorial Organic Synthesis, Library Screening Strategies, and Future Directions", *J. Med. Chem.* 37(10):1385–1401 (May 13, 1994).
Hobbes Dewitt et al., "'Diversomers': An approach to nonpeptide, nonoligomeric chemical diversity", *Proc. Natl. Acad. Sci. U.S.A.* 90:6909–6913 (Aug. 1993).
Horuk, "Molecular properties of the chemokine receptor family", *TIPS* 15:159–165 (May 1994).
Janda, "Tagged versus untagged libraries: Methods for the generation and screening of combinatorial chemical libraries", *Proc. Natl. Acad. Sci. U.S.A.* 91:10779–10785 (Nov. 1994).

(List continued on next page.)

*Primary Examiner*—Jyothsna Venkat
*Assistant Examiner*—Maurie E. Garcia
(74) *Attorney, Agent, or Firm*—Townsend and Townsend and Crew LLP

(57) ABSTRACT

This invention features methods of biphasic synthesis for synthesizing combinatorial libraries and combinatorial libraries of chemical compounds utilizing the template, and combinatorial libraries of chemical compounds formed by the methods of this invention.

2 Claims, 8 Drawing Sheets

OTHER PUBLICATIONS

Krepinsky et al., "Polymer–Supported Solution Synthesis of Oligosaccharides", *J. Am. Chem. Soc.* 113:5095–5097 (1991).

Look et al., "Methods for Combinatorial Organic Synthesis: The Use of Fast $^{13}$C NMR Analysis for Gel Phase Reaction Monitoring", *J. Org. Chem.* 59:7588–7590 (1994).

Metzger et al., "Ion–Spray Mass Spectrometry and High–Performance Liquid Chromatography—Mass Spectrometry of Synthetic Peptide Libraries", *Angew. Chem., Int. Ed. Engl.* 32(6):894–896 (1993).

Moser et al., "Interleukin–8 Antagonists Generated by N–terminal Modification", *J. Biol. Chem.* 268(10):7125–7128 (1993).

Pavia et al., "The Generation of Molecular Diversity", *Bioorg. Med. Chem.* 3(3):387–396 (1993).

Peterson, "A Simple Approach to Small Molecule Synthetic Libraries for Drug Discovery and Directed Chemical Analoguing", *Exploiting Molecular Diversity: Small Molecule Libraries for Drug Discovery*, Conference —La Jolla, CA (Jan. 23–25, 1995).

Pirrung et al., "Preparation and Screening against Acetylcholinesterase of a Non–Peptide 'Indexed' Combinatorial Library", *J. Am. Chem. Soc.* 117:1240–1245 (1995).

Rajarathnam et al., "$_1$H NMR Studies of Interleukin 8 Analogs: Characterization of the Domains Essential for Function" *Biochem* 33:6623–6630 (1994).

Ruoslahti, "Integrins", *Clin. Invest.* 87:1–5 (1991).

Ruoslahti et al., "New Perspectives in Cell Adhesion: RGD and Integrins", *Science* 238:491–497 (1987).

Singh et al., "Chemistry and Biological Activity of Thiazolidinones", *Chem. Rev.* 81:175–203 (1981).

Smith et al., "Synthesis and Biological Evaluation of a Library Containing Potentially 1600 Amides/Esters. A Strategy for Rapid Compound Generation and Screening.", *Bioorg. Med. Chem. Lett.* 4(24):2821–2824 (1994).

Stevanovic et al., "Natural and Synthetic Peptide Pools: Characterization by Sequencing and Electrospray Mass Spectrometry" *Bioorg. Med. Chem. Lett.* 3(3):431–436 (1993).

Terrett et al., "Combinatorial Synthesis —The Design of Compound Libraries and their Application to Drug Discovery", *Tetrahedron* 51(30):8135–8173 (1995).

Weller et al., "Fibrinogen receptor antagonists —a novel class of promising antithrombotics", *Drugs of the Future* 19(5):461–476 (1994).

Youngquist et al.,, "Matrix–assisted Laser Desorption Ionizatin for Rapid Determination of the Sequences of Biologically Active Peptides Isolated from Support–bound Combinatorial Peptide Libraries", *Rapid Communications In Mass Spectrometry* 8:77–81 (1994).

\* cited by examiner (g)

(j)

(h)

(k)

(i)

(l)

(s)

(v)

(t)

(w)

(u)

(x)

(y)

(z)

(aa)

(bb)

(ee)

(cc)

(ff)

(dd)

SCHEME I

LIQUID PHASE PARALLEL SYNTHESIS OF CHEMICAL LIBRARIES

RELATED APPLICATION

This application claims priority to Cheng and Saunders, LIQUID PHASE PARALLEL SYNTHESIS OF CHEMICAL LIBRARIES, provisional application Ser. No. 60/029,506, filed on Nov. 29, 1996, incorporated herein by reference including drawings.

BACKGROUND OF THE INVENTION

Two approaches have been used in efforts to discover novel chemicals useful in medicine, agriculture, or basic research. In the first approach of rational design, researchers perform structural studies to determine the three-dimensional structure of a target molecule in order to design compounds which are likely to interact with that structure. In the second approach, large libraries of compounds are screened for a desired biological activity. Compounds exhibiting activity in these screening assays become lead chemical compounds. Further study of compounds with structural similarity to the lead compounds can then lead to the discovery of other compounds with optimal activity.

Although traditional screening assays have focused on the screening of naturally occurring compounds, the ability to synthesize large combinatorial libraries of compounds with diverse structures has greatly increased the number of compounds available for screening. In combinatorial chemistry, each reactant from a first group of reactants is reacted with each reactant from a second group of reactants to yield products containing all the combinations possible from the reaction. If desired, all of the products from the first reaction are then reacted with each reactant from a third group of reactants to yield a large array of products. Additional reactions, if desired, can further increase the size of the library of compounds. Where it is desirable to use protection/deprotection protocols to prevent reactive groups from participating in a given reaction step, typically the same protocols are used for each compound in the growing library.

The generation and use of combinatorial chemical libraries for the identification of novel lead compounds or for the optimization of a promising lead candidate has emerged as a promising and potentially powerful method for the acceleration of the drug discovery process. (Terrett, N. K., et al., Tetrahedron 51:8135 (1995); Gallop, M. A., et al., J. Med. Chem. 37:1385 (1994); Janda, K. D., Proc. Natl. Acad. Sci. U.S.A. 91:10779 (1994); Pavia, M. R. et al., Bioorg. Med. Chem. Lett. 3:387 (1993)).

Combinatorial chemistry preferentially employs generally applicable reaction strategies and protocols which provide high-yielding reaction products. Various approaches to the synthesis of diverse chemical libraries have been disclosed including several methods utilizing solid supports. E.g., Bunin, B. A. & Ellman, J. A., J. Am. Chem. Soc. 114:10997–10998 (1992); Hobbes Dewitt, S., et al., Proc. Natl. Acad. Sci. USA 90:6909–6913 (1993); Chen, C., et al., J. Am. Chem. Soc. 116:2661–2662 (1994); Backes, J. B. & Ellman, J. A., J. Am. Chem. Soc. 116:11171–1172 (1994). Solid phase polymer-supported synthesis employs an insoluble matrix substrate upon which molecules in a combinatorial library may be assembled.

In solid support synthesis, a first reactant is linked to a solid support. This linkage may include a spacer linker arm connecting a functional group on the first reactant to a functional group on the solid support. Reaction of the first reactant bound to the solid support with a second reactant produces a desired product which is bound to the solid support, while unreacted second reactant remains unbound in solution.

If desired, additional reactants can be added to the product of the first reaction in subsequent reactions. The insoluble matrix substrate is washed after each elongation step. The products are then pooled and split into a second or subsequent set of parallel reaction vessels for further elongation as desired.

Some of the features of solid phase synthesis responsible for its widespread use in chemical synthesis are its repetitive coupling reactions as well as ease of product isolation and sample manipulation. Because the growing product is bound to the solid support, unreacted reactants can be easily removed by washing and/or filtration after each reaction in the synthesis of the final product. Furthermore, because of the ease of removal of unreacted reactants, the synthesis and separation of product from unreacted reactants can be automated. In addition, the ability to isolate the resin bound product by simple filtration permits the use of large reagent excesses to obtain high yields which are required for each step of a multistep synthesis.

In part, because of these features of solid phase synthesis, solution phase combinatorial synthesis has not yet gained wide acceptance as an alternative to solid phase synthesis. There have been, however, reports of solution phase, single-step amide, ester or carbamate condensations in the preparation of library mixtures. (Pirrung, M. C. and Chen, J. J. Am. Chem. Soc. 117:1240 (1995); Smith, P. W., et al., Bioorg. Med. Chem. Lett. 4:2821 (1994); Peterson, J. B. in *Exploiting Molecular Diversity: Small Molecule Libraries for Drug Discovery*, La Jolla, Calif., (Jan. 23–25, 1995).

Liquid phase synthesis has features which make it attractive for use in chemical synthesis. Liquid phase synthesis does not have the drawbacks associated with heterogeneous reaction conditions which can occur in solid phase synthesis. These drawbacks include nonlinear kinetic behavior, unequal distribution and/or access to the chemical reaction, solvation problems, the use of insoluble reagents or catalysts; and pure synthetic problems associated with solid phase synthesis. Liquid phase synthesis also does not have the restrictions of scale of reaction imposed by high cost and difficulty in handling large amounts of solid support necessary to obtain large quantities of product.

Liquid phase synthesis also does not require the use of specialized protocols for monitoring the individual steps of a multistep solid phase synthesis. (Egner, B. J., et al., J. Org. Chem. 60:2652 (1995); Anderson, R. C., et al., J. Org. Chem. 60:2650 (1995); Fitch, W. L., et al., J. Org. Chem. 59:7955 (1994); Look, G. C., et al., J. Org. Chem. 49:7588 (1994); Metzger, J. W., et al., Angew. Chem., Int. Ed. Engl. 32:894 (1993); Youngquist, R. S., et al., Rapid Commun. Mass Spect. 8:77 (1994); Chu, Y. H., et al., J. Am. Chem. Soc. 117:5419 (1995); Brummel, C. L., et al., Science 264:399 (1994); Stevanovic, S., et al., Bioorg. Med. Chem. Lett. 3:431 (1993)).

In solid phase synthesis, immobilized reactants which fail to react cannot be separated from immobilized reaction product intermediates. If the unreacted reactants participate in later reactions, they will give rise to a different undesired product than the intermediates, and the desired product will be released in an impure state. Thus, to be useful, each reaction in a solid phase synthesis must proceed with an unusually high efficiency. Optimization of the reactions to obtain the required reaction efficiencies is both time consuming and challenging. Even a modest level of purity in the final product (85%) pure requires a 92% yield at each step of a two-step reaction sequence, and a 95% yield at each step of a three-step reaction sequence. These high yields are not routinely available and require both an extensive investment in reaction optimization and/or a purification of the released solid phase product at each step. In addition, it may be necessary to use capping reactions at each step of the reaction to prevent the unreacted reactant from participating in subsequent reactions.

Because intermediates are not immobilized in liquid phase synthesis, liquid phase synthesis permits ease of sample manipulation, the purification of intermediates at each step, and a homogeneous reaction conditions. The non-limiting scale, expanded and nonlimiting repertoire of chemical reactions, direct production of soluble intermediates and final products for assay or for purification make solution phase combinatorial synthesis an attractive alternative to solid phase synthesis.

There is still a need, however, for a method of combinatorial synthesis which combines the advantages of both solid phase and liquid phase synthesis. Outside the field of combinatorial chemistry, biphasic oligomeric supports have been used for the serial synthesis of individual molecules.

In biphasic oligomer-supported liquid phase synthesis the growing product is attached to a large soluble polymeric group. The product from each step of the synthesis can then be separated from unreacted reactants by precipitating the oligomer attached to the growing product. Unreacted reactants can then be easily separated from the solid phase oligomer and attached product. This permits reactions to take place in homogeneous solutions, as well as eliminating tedious purification steps associated with traditional liquid phase synthesis.

Polyethylene glycol (PEG) is a conventional biphasic support employed in the area of serial chemistry due to its favorable physical and chemical properties. PEG polymers are available in a variety of molecular weights from 2,000 to 20,000 Dalton and can be purchased from commercial sources such as Fluka, Sigma and Aldrich (St. Louis, Mo.) as unprotected or protected, mono or difunctionalized polymers (e.g. the monomethyl ether of PEG).

PEG products remain soluble in most reaction mixtures and organic solvents (w/v: benzene 10%, $CCl_4$ 10%, Dioxane 10%, Methanol 20%, Pyridine 40%, $CHCl_3$ 47%, $CH_2Cl_2$ 53%, $H_2O$ 55%, EtOH 20% 34° C., EtOH 1% 32° C., EtOH 0.1% 20° C., diethylether 0.01%); yet, PEG can also be precipitated by exposure to diethyl ether. This permits easy separation of product from reactants, and subsequent crystallization in cold 20° C. ethanol. Unlike other polymers, PEG avoids the tendency to form gelatinous precipitates.

PEG has been employed as a biphasic support in connection with the serial synthesis and purification of oligonucleotides, oligosaccharides and peptides. The PEG is generally connected to the core molecule through an ester linkage (e.g. a free hydroxyl on PEG is esterified via a succinate linkage to a free hydroxyl on the core molecule). Amide linkages and ether linkages have also been used to link the PEG to the core molecule.

Methods for carrying out liquid phase synthesis of libraries of peptides and oligonucleotides coupled to a biphasic oligomeric support have been described. (Bayer, Ernst, et al., *Peptides: Chemistry, Structure, Biology,* 426–432; Bayer, Ernst & Mutter, Manfred, Nature 237:512–513 (1972); Bayer, Ernst, et al., J. Am. Chem. Soc. 96:7333–7336 (1974); Bonora, G. M. et al., Nucleosides and Nucleotides 10:269 (1991); Bonora, G. M., et al., Nucleic Acids Res. 8:3155–3159 (1990)).

Bayer & Mutter, supra, demonstrated the use of PEG as a biphasic support with respect to the synthesis of peptides. (Bayer et al., Nature 237:512 (1972).) Bayer & Mutter also discovered that the solubilizing power of PEG was sufficient to enable the synthesis of oligomers with chain lengths up to 12 residues. In addition, Bayer & Mutter noted that for short peptides of 10–15 amino acid residues, the physio-chemical properties of the PEG-bound peptides were governed not by the nature of the attached peptide, but by the nature of the polymeric ester group used as a linker (e.g., succinate linkage). PEG exhibits high retention of its crystalline phase after the attachment of short peptide blocks, but the physio-chemical properties of PEG-bound peptides for longer peptides (having more than 20 residues) strongly depended upon the primary sequence, side-chain protection and conformation of the attached peptide.

Bonora et. al., supra, carried out a large scale dideoxynucleotide synthesis using PEG as a biphasic support and obtained high yields above 90% for the synthesis of a octanucleotide with the sequence: d(TAGCGCTA). Nucleosides and nucleotides 10:269 ( 1991). Bonora also used a PEG biphasic support to synthesize cyclic oligodeoxyribonucleotides. (Bonora et al. Nucleosides and Nucleotides 12:21 (1993).)

Krepinsky et al. prepared milligram quantities of small PEG linked disccharides, utilizing the crystallization purification properties of PEG. (Krepinsky et al., J. Am. Chem. Soc. 113:5095 (1991).) Krepinsky et al. demonstrated that when the PEG was bound to a carbohydrate hydroxyl, the glycosylation reaction could be driven to virtual completion by repeated additions of the glycosylating agent. The excess reagents were subsequently washed off the precipitated PEG-bound product and the process was repeated until the desired length polymer was obtained. (Krepinsky et al., J. Am. Chem. Soc. 113:5095, 1991.)

PEG (polyethylene glycol) is a preferred biphasic support for serial syntheses due to its ease of precipitation and crystallization properties. However, alternative biphasic supports are also known in the serial chemistry area. Alternative biphasic supports include polyvinyl alcohol and polyvinylamine copolymerized with polyvinyl-pyrrolidone, etc. (Bayer et al., Nature 237:512 (1972).)

New methods of combinatorial chemistry which combine the advantages of liquid and solid phase synthesis will aid in drug discovery efforts.

Two biologically important peptides have been the focus of drug discovery efforts. The first peptide consists of a three amino acid sequence, arginine-glycine-aspartic acid. This peptide is also denoted by the single-letter amino acid code RGD. The RGD peptide is involved in cell attachment activities which play a role in diseases and conditions such as cardiovascular disease, cancer, osteoporosis, and inflammation. The second peptide consists of the sequence glutamic acid-leucine-arginine, denoted ELR. The ELR peptide is involved in conditions resulting from inflammatory responses such as rheumatoid arthritis, asthma, and acute respiratory distress syndrome (ARDS).

Interest in the RGD peptide has grown as the result of studies of the large glycoproteins from the extracellular matrix (ECM). The cell attachment activity of the most readily available ECM protein, serum fibronectin, has been found to reside in the RGD sequence. Subsequently, it was shown that a number of ECM proteins contain the RGD motif, and that the sequence is required for recognition and interaction of these proteins with the cell. (Ruoslahti et al., Science, 238:491, 1987.)

Further research revealed that immobilized synthetic peptides containing the RGD motif can mimic the cell attachment activity of ECMs. In addition, in solution these same peptides were capable of inhibiting cell attachment to other RGD-containing ligands. Thus, RGD-based therapeutics can potentially function either as agonists which promote the interaction of cells and tissues with artificial matrices containing the RGD-based drug, or as antagonists which inhibit cell-cell and cell-ECM interactions.

Abnormal ECM function has been associated with a number of diseases or conditions, such as cardiovascular disease, cancer, osteoporosis, and inflammation. For example, RGD plays an integral role in the formation of blood clots which can give rise to cardiovascular diseases.

Initial events in blood-clot formation, i.e., thrombus formation, frequently entail the activation of platelets by thrombogenic surfaces containing RGD sequences, and the subsequent aggregation of platelets onto these surfaces. A protein complex on the surface of platelet cells has been shown to interact with the RGD motif. Adhesion and aggregation of platelets is mediated by adhesive proteins that interact with the platelet membrane glycoprotein complex $\alpha\pi b\beta 3$ at the platelet surface. Platelet $\alpha\pi b\beta 3$ glycoprotein complex is a member of the family of cell adhesion receptors, called integrins. (Ruoslahti, E. J. Clin. Invest., 87:1, 1991.) It has been shown that, like several of the integrins, the $\alpha\pi\beta 3$ complex on activated platelets can bind to a RGD tripeptide sequence in several proteins including fibrinogen, fibronectin, von Willebrand factor, and vitronectin. Molecules containing the RGD motif or analogs of the RGD motif can inhibit the binding of fibrinogen to the $\alpha\pi b\beta 3$ complex on activated platelets.

The antithrombotic activity of many molecules that inhibit the $\alpha\pi b\beta 3$-fibrinogen interaction has been accessed in vitro and in vivo. Most of these compounds fall into four categories: RGD-based peptides (small linear and cyclic peptides containing the RGD sequence or its equivalent), (Cheng et al., J. Med. Chem. 37:1, 1994) snake venom peptides, monoclonal antibodies raised against $\alpha\pi b\beta 3$, and non-peptide fibrinogen receptor antagonists that mimic the RGD tripeptide sequence. (Weller et al., Drugs of the Future 19:461, 1994.)

The second peptide motif, ELR, is found in chemokines. Chemokines are small proteins having important roles in a wide range of acute and chronic inflammatory processes. The C-X-C chemokine family is characterized by a four cysteine motif, in which the first two cysteines are separated by a single intervening residue, the other two appearing elsewhere in the protein sequence (Horuk, R., TIPS 15:159 (1994).) In general, C-X-C chemokines are chemoattractants for neutrophils—white blood cells which are involved in inflammatory responses. Hence, C-X-C chemokines are considered to be the key mediators of inflammatory responses where neutrophil recruitment is involved. Interleukin 8, Il-8, is a potent inflammatory mediator that belongs to the C-X-C family which also includes MGSA (melanoma growth-stimulating activity) and NAP-2 (neutrophil activating peptide).

A specific tripeptide motif, ELR, occurs close to the N-terminus in all C-X-C chemokines that demonstrate biological activation of neutrophils. Although not the sole determinant for binding of the C-X-C chemokines to cellular receptors, the ELR motif is essential for the binding of the C-X-C chemokines to cellular receptor. (Moser, B. et al., J. Biol. Chem., 268:7125 (1993); Rajarathnam et al., Biochem., 33:6623 (1994) and Clark, Lewis I. et al., J. Biol. Chem. 266:23128 (1991).) Molecules which compete for the ELR binding site to the C-X-C chemokine receptor should antagonize the binding of the endogenous ligand and hence prove to be useful in the treatment of C-X-C chemokine driven diseases.

Thiazolidinones are another class of compounds of biological interest. They have been reported to possess a wide range of biological activities including antifungal, antibacterial, antihistaminic, antimicrobial, anti-inflammatory and antidiabetic activities. (Singh, S. P.; Parmar, S. S.; Raman, K.; Stenberg, V. I., Chem. Rev. 1981, 81, 175–203 and Berger, J.; Biswas, C.; Hayes, N.; Ventre, J.; Wu, M.; and Doebber, T. W., Endocrinology, 1995, 137, 1984.)

None of the references described herein is admitted to be prior art.

SUMMARY OF THE INVENTION

This invention relates generally to methods of liquid phase parallel synthesis of chemical libraries utilizing a template attached to a biphasic support, and the combinatorial libraries produced by such methods.

In a first aspect, this invention relates to a method of synthesizing a chemical library comprising the following steps:

(a) reacting, in solution, a template with a biphasic support to form a (biphasic support)-template;

(b) dividing said (biphasic support)-template into at least two portions;

(c) reacting each said portion of (biphasic support)-template with at least one reactant to form a functionalized (biphasic support)-template;

(d) precipitating each said portion of (biphasic support)-template;

(e) washing excess reactant from each said portion of functionalized (biphasic support)-template;

(f) dividing each said portion of functionalized (biphasic support)-template into at least two portions;

(g) repeating steps (c)–(f) at least once.

In liquid phase parallel synthesis, the biphasic support is soluble during all reactions involved in the synthesis but can be made insoluble during isolation and purification steps; thus, it provides both the advantages of solid phase synthesis and traditional liquid phase organic synthesis. Additionally, because the reactants and products are soluble during reactions, the reactions can be followed by NMR, thin layer chromatography (TLC), or HPLC.

A biphasic support is an oligomer or mixture of oligomers, each of which is soluble under all reaction conditions, e.g., solvent, temperature and pressure, involved in the synthesis but which can be made insoluble during isolation and purification steps. Biphasic supports combine advantages of solid phase synthesis, e.g., the clean and convenient separation of the oligonucleotide from the reaction mixture, reduced purification time, and the economical preparation of small oligonucleotides in milligram quantities, with advantages of liquid phase synthesis, e.g., monitoring by TLC or HPLC, greater selection of reagents, and greater variability of temperature and pressure conditions.

Templates suitable for combinatorial chemistry were previously described in U.S. application Ser. No. 60/006,891 entitled Template for Solution Phase Synthesis of Combinatorial Libraries, which is incorporated herein by reference. A template is a compound having a plurality of functionalization sites. Preferably the template contains sites which can be controllably functionalized with nucleophiles, acylating agents or electrophiles, enabling the synthesis of libraries with variable regions. Preferred embodiments of templates are shown in Structure 1 in Scheme 1 and Structure 1 in Scheme 2. In a particularly preferred embodiment, the template will be N-((tert-butyloxy)carbonyl) iminodiacetic acid (IDA). The template shown in Structure 1 of Scheme 1 is flexible, possessing 1–3 functionalizable sites for diversification and little inherent structural or conformational bias which might limit its use. The functionalizable sites are carboxylic acid groups, derivatives of carboxylic acid groups, or an amine. In the preferred embodiment shown in Structure 1 of Scheme 1, one of the functionalizable groups is a secondary amine protected by a butoxycarbonyl (BOC) group. The two other functionalizable sites groups are carboxylic acid groups converted to an anhydride, for example, by treatment in situ with 1-ethyl-3-(3-dimethylaminopropyl)carbodiimide) or DCC.

The template attached to a biphasic support polymer, i.e., a (biphasic support)-template, is designed to permit reaction products to be easily purified from unreacted reactants using solid/liquid extractions. The bond between a functionalizable group on the template and the biphasic support is preferably an ester or amide bond. Preferably the bond is an ester.

The compounds produced by combinatorial synthesis using the template will preferably be small organic molecules. Some compounds in the library may mimic the effects of non-peptide ligands or peptide ligands.

A template refers to a chemical compound having a densely functionalizable core. The densely functionalizable core may be symmetrical and impose little structural or conformational bias. Alternatively, it may be desirable for the densely functionalizable core to be asymmetrical so that the functionalization reactions will be regiospecific and/or stereospecific.

A densely functionalizable core is a chemical group which contains two or more functionalization sites attached to nearby atoms within the template. By "nearby atom" is meant preferably within 1 to 10 atoms, more preferably 1 to 6, even more preferably 2 to 5 atoms.

A reactant containing a functional group is capable of reacting with a functionalization site on the template. The reactants added to the functionalization sites of the template core provide molecular diversity and, as such, libraries built upon a template may prove widely applicable to many, if not all, biological targets.

To form a (biphasic support)-template, the biphasic support is reacted with a functionalization site on the template.

Chemical modification of the (biphasic support)-template or core molecule results in the generation of a "multifunctionalized (biphasic support)-template" or "multifunctionalized product". A "multifunctionalized product" is a (biphasic support)-template molecule which has been reacted with two or more reactants, each containing a functional group capable of reacting with a functionalizable group on the template, wherein the functional groups may be the same or different from each other. Furthermore, a reactant may contain an additional functionalizable group blocked with a protecting group.

The multifunctionalized product is functionally equivalent to a multi-subunit compound. For instance, where a template has been reacted with two reactants and released from the biphasic support, the multifunctionalized product may be functionally equivalent to a three subunit compound, such as a tripeptide, without the need for protection and deprotection steps. This is in contrast to typical methods of synthesis of peptides in which, due to the need for protection and deprotection steps, the synthesis of a trimer containing three subunits would require six to nine steps.

A (biphasic support)-template to which one reactant has been added to one functionalization site is referred to as a "first-modified (biphasic support)-template" or "first modified product." A (biphasic support)-template to which reactants have been added to two functionalization sites is referred to as a "second-modified (biphasic support)-template" or "second-modified product." A template to which more than three reactants have been added is similarly referred to by the term "n-modified (biphasic support)-template" "n-modified product", where n is the number of reactants which have been added to functionalization sites on the template, including functionalization sites introduced during earlier reactions.

Preferably the template will contain three functionalization sites which can be differentially reacted with a biphasic support or reactants containing functional groups.

More specifically, the biphasic support polymer attached to the template is polyethylene glycol (PEG) that is soluble in the reaction media, but can be precipitated selectively for isolation and purification purposes. Precipitation permits removal of excess reagents and byproducts by simple filtration.

A reactant is any chemical which can undergo a chemical reaction to form a new bond. Because the functionalization sites, reactants and the reaction conditions are not limited, templates can be designed for use with a very broad spectrum of chemical reactions. Because of the variability permitted by the choice of reactants, use of a template having three functionalization sites, where one of the sites is bound to the biphasic support, enables the synthesis of combinatorial libraries with at least two variable groups. Where at least one reactant contains additional groups which can serve as functionalization sites, the compounds in a combinatorial library synthesized using a template initially containing three functionalizable groups may have more than two variable groups.

Preferably, the reactant will be selected from nucleophiles or electrophiles, such as acylating agents, amines, carboxylic acids, amides, esters, thioesters, L-amino acids, D-amino acids, synthetic amino acids, nucleotides, sugars, lipids, or carbohydrates. In addition, the reactants may contain additional chemical groups such as a carbon-hetero multiple bond, heterocycles, ethers, aromatic groups, or a group which can act as an additional functionalization site. Where the reactant contains a group which can act as an additional functionalization site, preferably the functionalizable group will not be reactive in the reaction in which the reactant is added to the template. For instance, the additional functionalizable group may be blocked by a protecting group such as BOC or Fmoc, or may be less reactive than the functional group undergoing reaction. For instance, primary amines are more reactive than alcohols.

Where the functionalization site is an electrophile, e.g., an anhydride or other activated carboxylic acid derivative, the reactant will be a nucleophile. An electrophile is a chemical compound which is seeking electrons. A nucleophile is an electron rich compound, and may carry a formal charge or be partially charged through polarization of a chemical bond.

Functionalization site refers to a chemical group capable of undergoing a chemical reaction with a functional group of a reactant in which a bond is formed between the functionalization site and the functional group on the reactant. A functionalization site may be present as a reactive functionalization site which is capable, without an additional chemical reaction, of reacting with a reactant. Alternatively, a functionalization site may be present in an unreactive form which is attached to a blocking group in order to prevent reaction of the functionalization site in a given reaction step. The blocking group can be removed prior to a later reaction step, liberating the functionalization site in a reactive form suitable for reaction with a reactant. The activated form of the functionalization site is preferably a nucleophile or an electrophile. Even more preferably, the functionalization site is an electrophile containing a carbonyl group. Alternatively, even more preferably a functionalization site will be a nucleophile containing an amine.

Still more preferably, where the functionalization site is an electrophile, the functionalization site may be an activated carboxylic acid derivative or an anhydride. An anhydride contains both a reactive functionalization site, and a protected functionalization site which is released upon reaction of the anhydride to yield a functionalized acyl group and a carboxylate functionalization site. For purposes of this application, an anhydride chemical group will be considered to contain two functionalization sites.

The reaction between a functionalization site and a reactant is an organic chemical reaction.

Preferably, where the functionalization site is electrophilic, the reaction will be a nucleophilic acyl substitution.

The bond formed by the chemical reaction may be, for example, ester $[R^1C(O)OR^2]$, thioester $[R^1C(O)SR^2]$, or amide $[R^1C(O)N(R^2)R^3]$ (where each $R^1$, $R^2$, and $R^3$ may be the same or different, cyclic or acyclic; may be, for example, hydrogen, alkyl, alkenyl, alkynyl, ether, heterocyclic, or aryl. Where the functionalization site is a nucleophilic group, the reaction will preferably be an acylation reaction. Preferably the bond formed by the chemical reaction will be an amide.

The chemical synthesis will preferably involve two or more sequential reaction steps. Preferably, at each step, one reactant forms a bond with one functionalization site on the template. In addition, reactants may contain additional functionalization sites which participate in additional reaction steps with additional reactants. A reaction step refers to one reaction in a series of reactions.

At each reaction step, preferably portions or aliquots of (biphasic support)-template or functionalized (biphasic support)-template will be individually reacted with a set of reactants to form a set of n-modified multifunctionalized products.

Preferably, separation of desired products from unreacted reactant and other reagents is performed following each reaction, before proceeding to the next reaction step. Preferably this separation is a solid phase/liquid phase extraction performed after precipitation of the biphasic support. To facilitate solid/liquid extractions, it is preferred that the reactants remain soluble under the conditions used to precipitate the biphasic support.

The precipitate should also be easily separated from the liquid phase, for instance, by trapping the precipitate on the opposite side of a barrier containing openings of a size sufficient to completely block the flow of the solid support, while permitting the liquid phase and any soluble compounds in the liquid phase to readily pass through the openings. For example, the barrier may be a filter membrane.

In a second aspect, the invention relates to combinatorial libraries formed by carrying out the method of this invention.

A "chemical library" is a collection of compounds in which the compounds comprising the collection are composed of one or more types of subunits. The subunits may be selected from natural or unnatural moieties, including nucleophilic compounds, acylating agents, aromatic compounds, heterocyclic compounds, ethers, amines, carboxylic acids, amides, esters, thioesters, compounds containing a carbon-hetero multiple bond, L-amino acids, D-amino acids, synthetic amino acids, nucleotides, sugars, lipids, carbohydrates.

The compounds of the combinatorial library differ in one or more ways with respect to the number, order, type or types of, or modifications made to, one or more of the subunits comprising the compounds. Alternatively, a combinatorial library may refer to a collection or set of "modified" or "functionalized" templates which vary as to the number, type or position of R or functional groups they contain and/or identity of molecules composing the template. The collection of compounds is generated in a systematic way. Any method of systematically generating a collection of subunits differing from each other in one or more of the ways set forth above is a combinatorial library.

A (biphasic support)-template is thus useful for rapidly generating and developing drug candidate molecules. In particular, the (biphasic support)-iminodiacetic acid template is useful in generating compounds which are agonists or antagonists of the ELR or RGD peptides, and in later optimizing those candidates that show the most interesting biological behavior.

The (biphasic support)-templates and methods can be easily adapted for use in automated chemical synthesis of libraries of molecules with diverse structures. One such device is described in Brenner, U.S. patent application Ser. No. 08/281,194 filed Jul. 26, 1994, hereby incorporated by reference.

The combinatorial libraries generated by the methods of the present invention may be screened for pharmacologically active compounds, such as peptide analogs of RGD and ELR motifs. By pharmacologically active is meant that a compound may affect the functioning of a physiological process, such as cell attachment activity or neutrophil activation, signal transduction by a cellular receptor, initiation, cessation or modulation of an immune response, modulation of heart function, nervous system function, or any other organ or organ system. A pharmacologically active compound may also inhibit an endogenous enzyme involved in a pathogenic process, or block a binding interaction involved in a pathological process, such as a DNA/protein interaction or a protein/protein interaction. In addition, a pharmacologically active compound may stimulate or inhibit the activity of a bacteria, virus, fungus, or other infectious agent. A pharmacologically active compound may also modulate the effects of a disease, that is, to prevent or decrease the severity of, or cure a disease such as cancer, diabetes, atherosclerosis, high blood pressure, Parkinson's disease and other disease states. Screening for pharmacological activity may be performed as would be known in the art. Preferably, the compounds will affect cell attachment activity or neutrophil activation.

Compounds which have been shown to be pharmacologically active compounds may be formulated for therapeutic administration as described in detail below.

The combinatorial libraries generated by the methods of the present invention may also be screened for diagnostically useful compounds. By diagnostically useful is meant that the compound can be used to indicate the presence of a particular disease in a human or animal.

In a preferred embodiment, the combinatorial library of this invention consists of an array of molecules having the formula shown as Structure [5] in Scheme 1 shown in FIG. 2. In a preferred embodiment, $R^1$ has a formula selected from the following formulas:

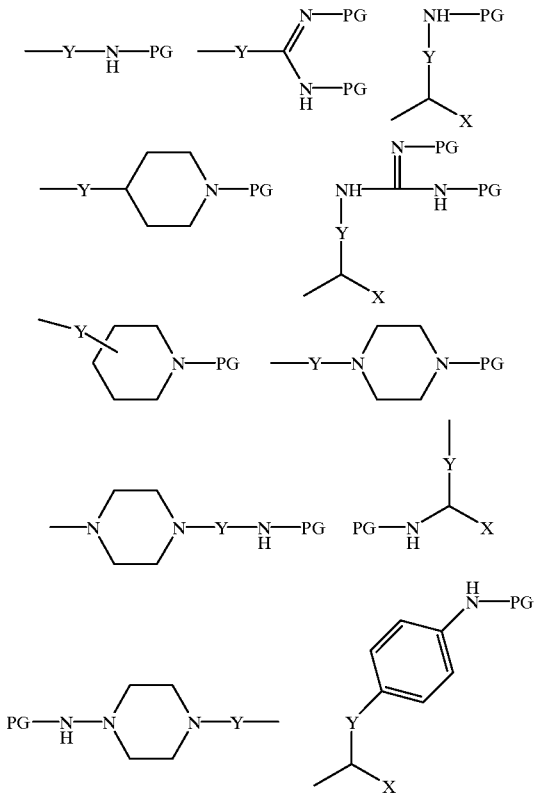

wherein Y is selected from the group consisting of alkyl, aryl; heteroaryl; heterocyclic; cycloalkyl, and cycloalkenyl;

the protecting group (PG) is selected from the group consisting of benzyloxycarbonyl (CBZ), 2-bromobenzyloxycarbonyl, 2-chlorobenzycarbonyl, 9-toluenesulfonyl, mesitylene-2-sulfonyl, and tert-butyloxcarconyl, t-butoxycarbonyl (BOC), or 9-fluorenylmethoxycarbonyl (Fmoc);

X is selected from the group consisting of COO-$PG_1$, wherein $PG_1$ is selected from the group consisting of benzyl, methyl, 2-adamantyl, cyclohexyl, 9-fluorenylmethyl, tert-butyl, 1-adamantyl, 4-methoxy-2,3,6-trimethyl benzensulfonyl, and 1,2,2,5,7,8-pentamethylchroman-6 sulfonyl;

$R^2$ is selected from the group consisting of aryl, alkyl, wherein aryl is a mono- or polycyclic aromatic system comprised of 5 or 6 membered rings containing 0, 1, 2, 3, or 4 heteroatoms selected from nitrogen, oxygen and sulfur, which may be unsubstituted or substituted, wherein the substituents may be one or more groups selected from hydroxyl, halogen, cyano, trifluoromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$alkyl, or hydroxycarbonyl$C_{1-5}$alkoxy;

wherein alkyl is $C_{1-10}$alkyl, either unsubstituted or substituted, with one or more groups selected from halogen, hydroxyl, $C_{1-5}$alkycarbonylamino, aryl$C_{1-5}$alkyl carbonylamino, aryloxy, $C_{1-5}$alkoxy, $C_{1-5}$alkoxycarbonyl, $C_{0-5}$alkylaminocarbonyl, $C_{1-5}$alkylcarbonyloxy, $C_{3-8}$cycloalkyl, aryl, oxo, amino, $C_{1-6}$alkyl, $C_{1-3}$alkylamino, aryl$C_{0-5}$alkylaminocarbonyl, phenyl$C_{1-3}$alkylamino, aminocarbonyl$C_{0-4}$alkyl, hydroxycarbonyl $C_{0-5}$alkyl, $C_{1-8}$alkylsulfonylamino, aryl$C_{0-10}$alkylsulfonylamino, $C_{1-8}$alkyl-sufonyl, aryl$C_{0-10}$alkylsulfonyl, $C_{1-5}$alkyloxycarbonylamino, aryl$C_{1-5}$alkyloxycarbonylamino, or aryl$C_{1-5}$alkyloxy.

In a more preferred embodiment, $R^1$ is selected from the following compounds:

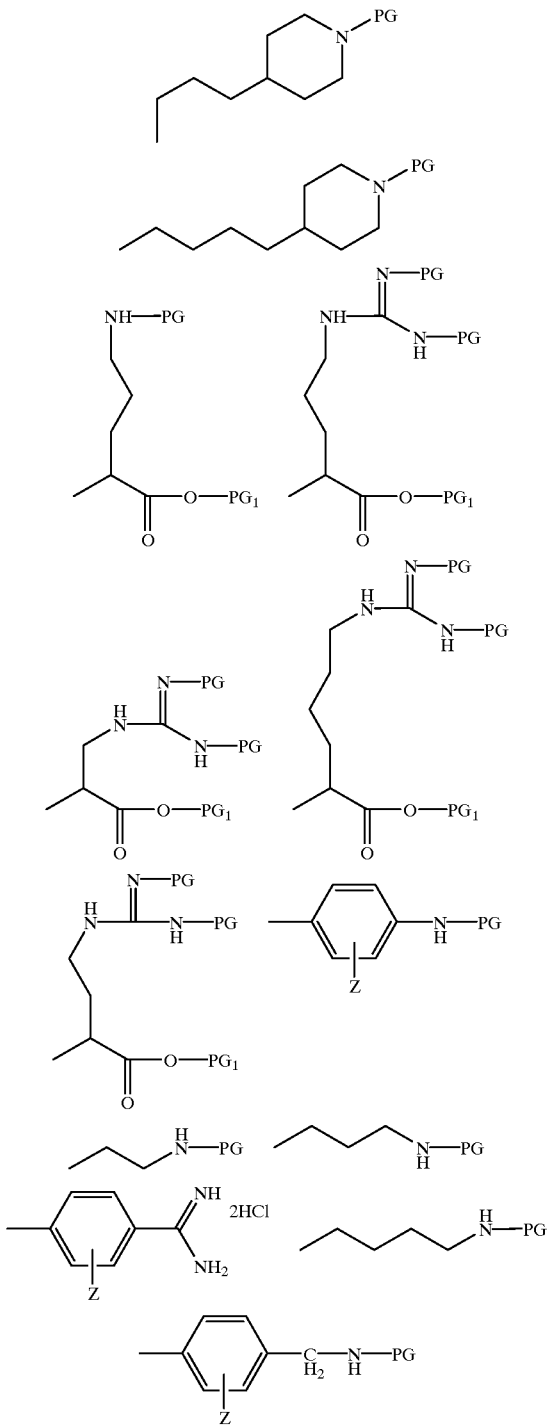

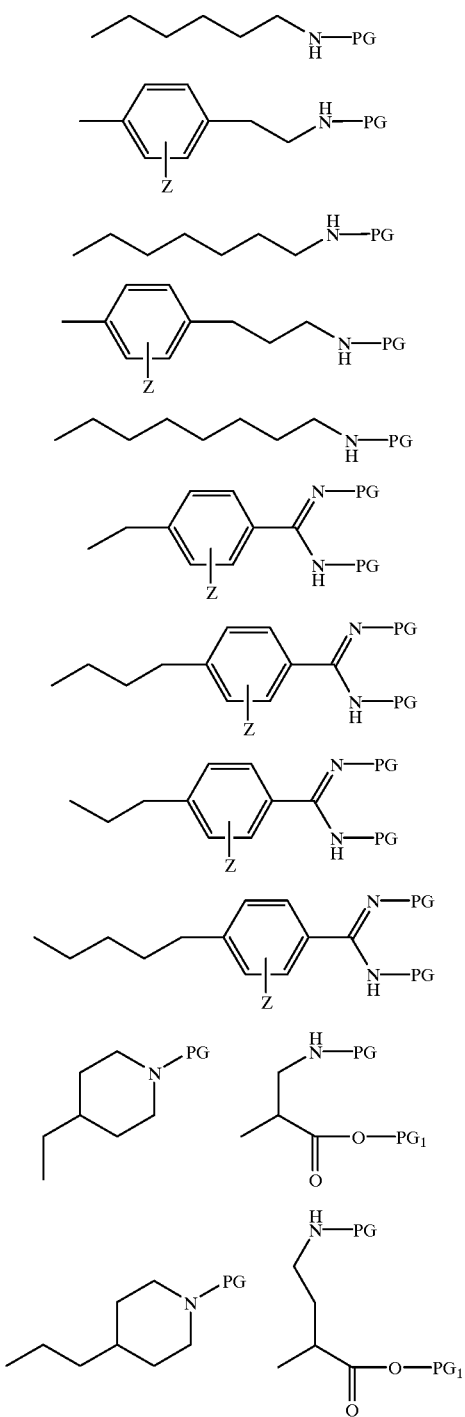

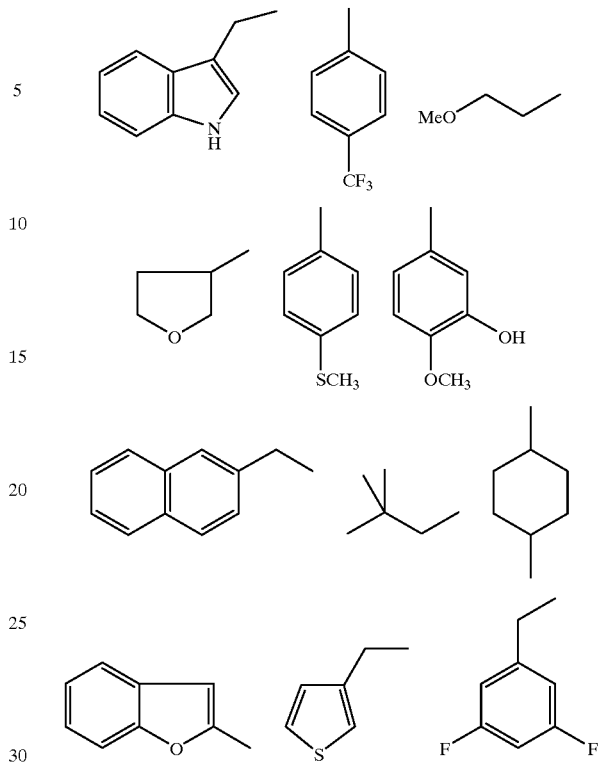

wherein Z is selected from the group consisting of hydroxyl, halogen, cyano, trifluromethyl, $C_{1-3}$alkoxy, $C_{1-5}$alkyl, $C_{1-5}$alkylcarbonyloxy, nitro, $C_{1-5}$alkoxycarbonyl, amino$C_{1-5}$alkyl.

In a still more preferred embodiment, R1 is selected from the following group of compounds and R2 is selected from the following group of compounds:

Still another aspect of this invention is a method of generating a (biphasic support)-template for combinatorial synthesis including the step of treating an iminodiacetic acid having a protected amine group with polyethylene glycol monomethyl ether to form a monoacid. The amine group may be protected, for example with BOC.

The (biphasic support)-templates of this invention are particularly useful in facilitating the separation of unreacted reactants or catalysts from the desired product in liquid phase chemical reactions. The methods of this invention utilize the (biphasic support) templates to synthesize functionalized products which are easily separated from unreacted reactants in a solid phase/liquid phase extraction.

Other advantages result from carrying out the reactions in a solution. For instance, reaction in a homogeneous solution can give rise to broader range of products compared with methods of solid phase synthesis. Still another advantage of the template is the ease of scaling up a reaction which takes place in a homogeneous liquid phase.

Use of the template also facilitates separation of the desired product from failure products which failed to react at critical steps of the synthesis. In syntheses employing the template, chemical reactions occur in solution, yet unreacted reactants are easily separated from products by use of liquid/solid phase extractions.

In addition, when the product is in the liquid phase, the completeness of the reaction can be monitored by taking aliquot volumes and analyzing the aliquots, e.g., by nuclear magnetic resonance, or by non-destructive spectrophotometric methods such as TLC or HPLC.

Other and further objects, features and advantages will be apparent from the following description of the presently preferred embodiments of the invention.

DETAILED DESCRIPTION OF THE INVENTION

This invention relates to compounds and methods for the chemical synthesis of organic compounds.

In one preferred embodiment, this invention describes a (biphasic support)-template having a plurality of functionalization sites. Preferably the template contains three sites which can be controllably functionalized with nucleophiles, acylating agents or electrophiles. The biphasic support binds to one of the functionalizable sites, enabling the synthesis of libraries with at least two variable regions.

In some preferred embodiments, the template may have a structure which imposes structural or conformational bias. In other preferred embodiments, the template may be symmetrical so that the template imposes little structural or conformational bias.

Preferably two of the functionalization sites on the template are blocked by a protecting group during the first reaction to form the (biphasic support)-template, in order to insure that only one of the functionalization sites is functionalized during the reaction with the biphasic support. A protecting group is any chemical group covalently bonded to a protected functionalization site group which prevents the functionalization site group from participating in the chemical reactions used to modify other functionalization sites. Protecting groups may include protecting groups traditionally used in the synthesis of peptides or oligonucleotides, such as t-butoxycarbonyl (BOC), or 9-fluorenylmethoxycarbonyl (Fmoc), benzyloxycarbonyl, 2-bromobenzyloxycarbonyl, 2-chlorobenzycarbonyl, 9-toluenesulfonyl, or mesitylene-2-sulfonyl. In addition, protecting groups may include a group within the same molecule to which the protected functionalization site group is covalently bonded, e.g., the activated acyl group in an anhydride acts as a protecting group for the other acyl group in an anhydride. The reaction should tolerate any number of protecting groups on nitrogen, as would be known to one of ordinary skill in the art, for example, BOC or Fmoc. More generally, any protecting group which does not interfere with reaction of the unprotected functionalization sites of the template may be utilized.

A protecting group may either become detached from the functionalization site group during the reaction of an unprotected functionalization site group, or the protecting group may be removed in a separate reaction prior to modification of the protected functionalization site group.

Figure 2:
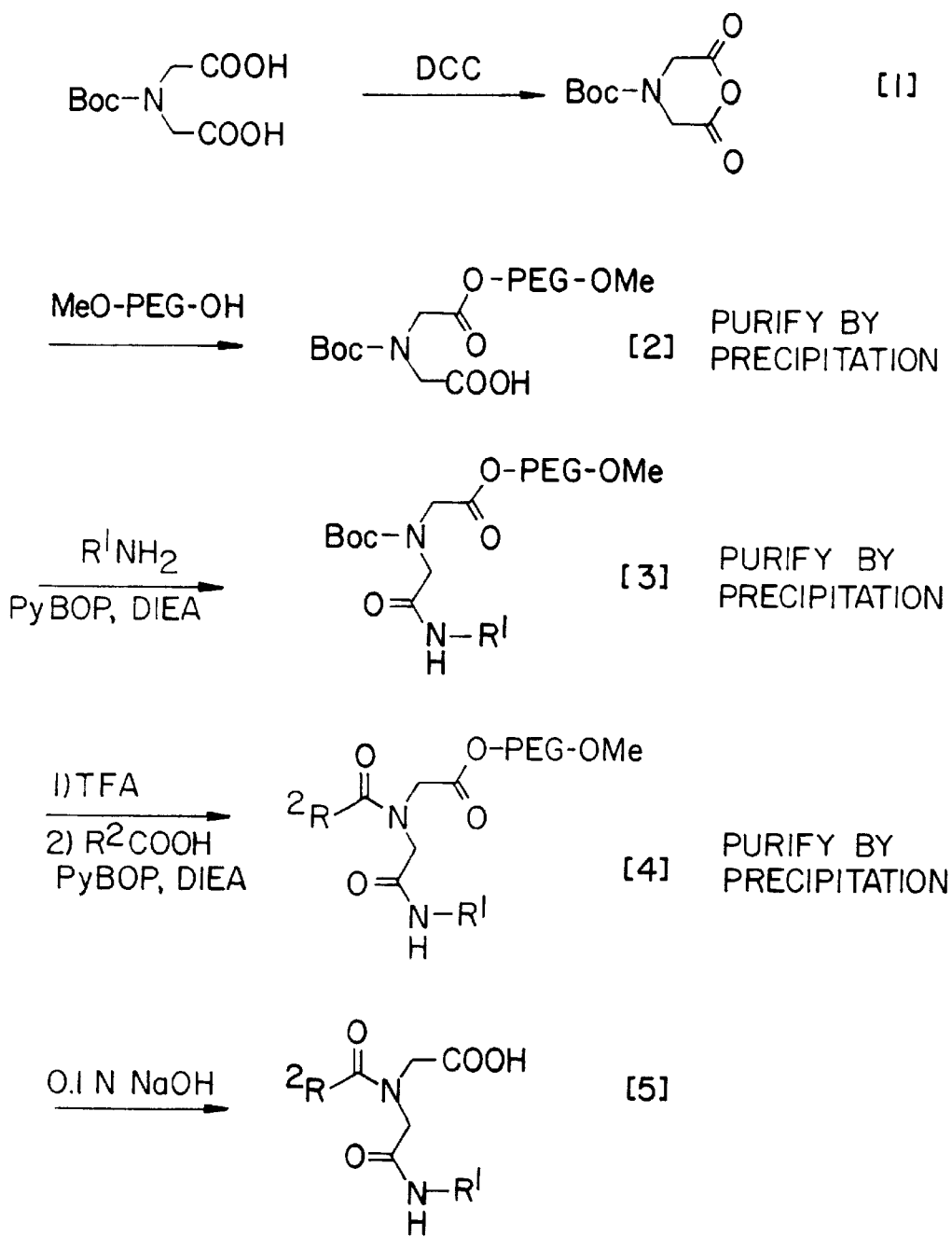
FIG. 2 illustrates a preferred embodiment of a reaction scheme for the synthesis of a combinatorial library in which PEG-monomethyl ether is reacted with a N-((tert-butyloxy)carbonyl)iminodiacetic acid anhydride template to form a PEG-template. The PEG-template is then reacted with $R^1NH_2$, followed by reaction of the PEG-template-$NHR^1$ with $R^2COOH$. The PEG is then removed by saponification.
Figure 3:
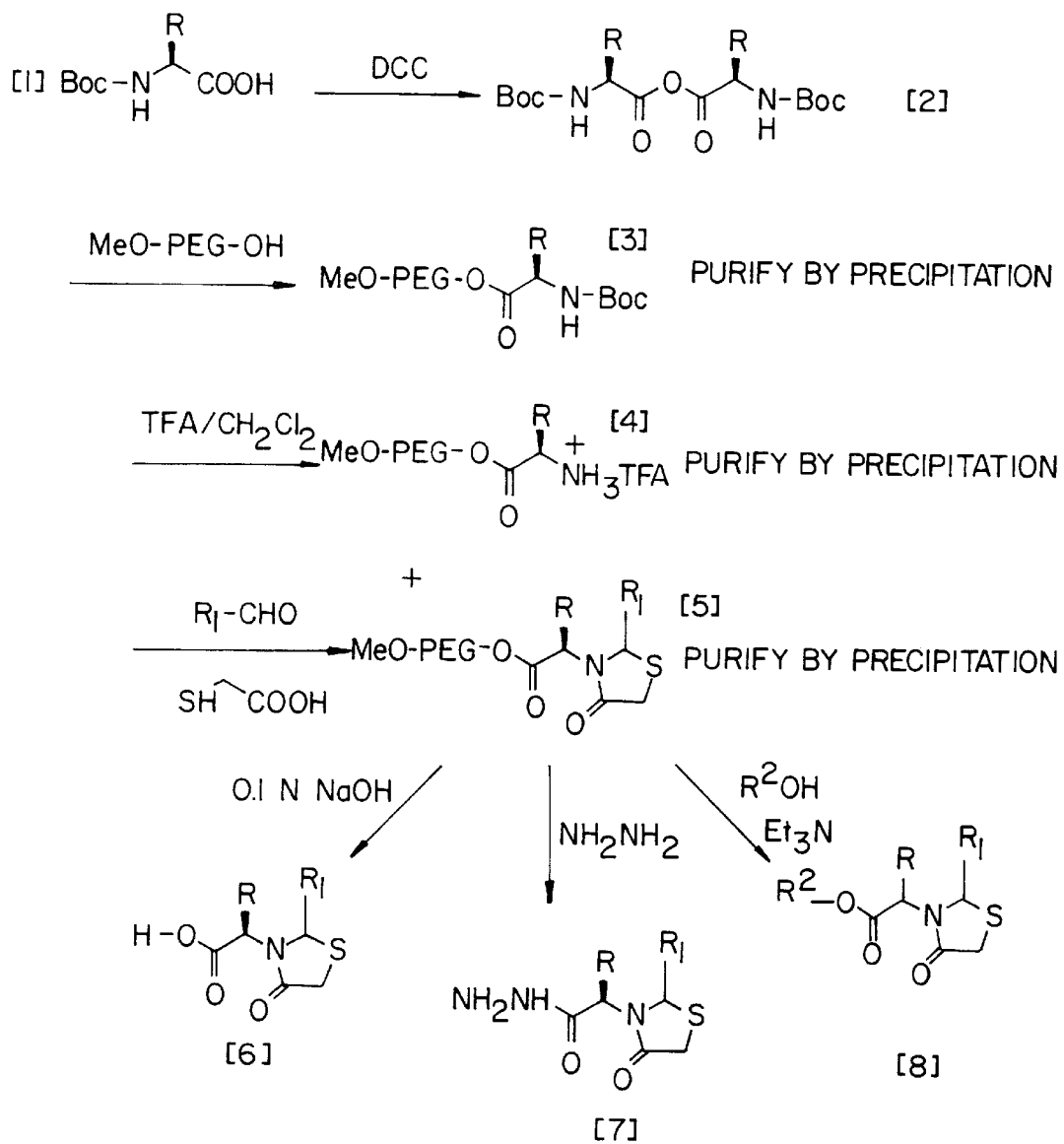
FIG. 3 shows another preferred embodiment of the synthesis of a combinatorial library.

One preferred embodiment of a (biphasic support)-template is derived from the reaction of PEG-monomethyl ether with N-((tertbutyloxy)carbonyl)iminodiacetic acid, as shown in Scheme 1 in FIG. 2. The template shown in Scheme 1 is flexible, possessing 1–2 functionalizable sites for diversification and little inherent structural or conformational bias which might limit its use. The functionalizable sites are carboxylic acid groups, derivatives of carboxylic acid groups, or an amine. In the preferred embodiment shown, one of the functionalizable groups is a secondary amine protected by a butoxycarbonyl (BOC) group. The two other functionalizable sites groups are carboxylic acid groups converted to an anhydride, for example, by treatment in situ with 1-ethyl-3-(3-dimethylaminopropyl)carbodiimide) (EDCI) or DCC (dicyclohexylcarbodiimide).

Another preferred embodiment of this invention is a method of generating a (biphasic support)-template for combinatorial synthesis including the step of treating an iminodiacetic acid having a protected amine group with EDCI or DCC in situ to form a protected iminodiacetic acid anhydride, followed by reaction with PEG-monomethyl ether. A method of generating the PEG-template in FIG. 2 from N-BOC-iminodiacetic acid is described below in Example 1.

In another preferred embodiment, this invention features a method of synthesizing a combinatorial library comprising the following steps:

(a) reacting, in solution, a template with a biphasic support to form a (biphasic support)-template;

(b) dividing said (biphasic support)-template into at least two portions;

(c) reacting each said portion of (biphasic support)-template with at least one reactant to form a functionalized (biphasic support)-template;

(d) precipitating each said portion of functionalized (biphasic support)-template;

(e) washing excess reactant from each said portion of functionalized (biphasic support)-template;

(f) dividing each said portion of functionalized (biphasic support)-template into at least two portions;

(g) repeating steps (c)–(f) at least once.

For example, in a first set of reactions, separate aliquots of reaction mixture containing the template are individually reacted with one of first reactants $A_2 \ldots A_n$ to yield a set of first modified products, each containing a functional group at the first functionalization site, which can be the same or different.

In a preferred series of functionalization reactions carried out with the preferred embodiment of the template (a symmetrical molecule containing anhydride and protected secondary amine functionalization sites), the first reaction will be an attachment reaction. The anhydride group in this embodiment of the template contains one acyl group which is susceptible to an attachment reaction. During the attachment reaction, a nucleophile on the biphasic support attacks one acyl group of the anhydride, displacing the second acyl group, which leaves as a carboxylic acid group. The reaction therefore simultaneously results in formation of the (biphasic support)-template bond between one of the carboxyl groups of the anhydride and liberation of the second carboxylic acid as the first functionalization site ($—CO_2H$). The nucleophile on the biphasic support will preferably be an alcohol, amine, or thiol.

In a second reaction step, a reactant, preferably an alcohol, amine, thiol or nucleophile is reacted with the free carboxylic acid to convert the carboxylic acid to, for example, an amide, ester, thioester, or other derivative of a carboxylic acid. For example, the carboxylic acid may be reacted with a primary amine in the presence of diisopropyl ethylamine and PYBOP to form an amide.

In a preferred set of reactions using a preferred embodiment of the PEG-template shown as Structure 2 in Scheme 1 in FIG. 2, the first set of reactants reacted with the PEG-template have the formula $R^1NH_2$, wherein $R^1NH_2$ is preferably selected from the compounds in Table 1:

Table 1

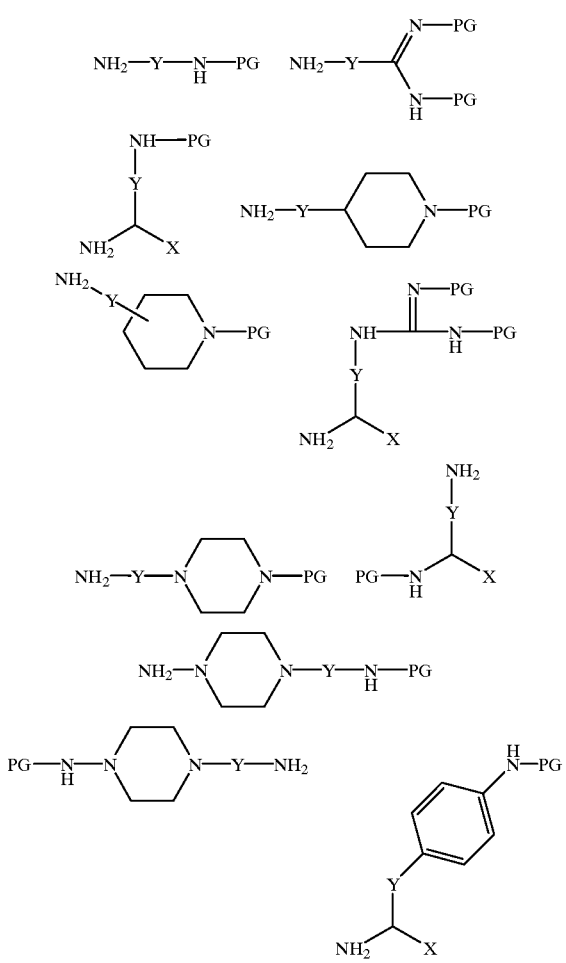

and wherein Y is selected from the group consisting of alkyl, aryl; heteroaryl; heterocyclic; cycloalkyl, and cycloalkenyl;

the protecting group (PG) is selected from the group consisting of benzyloxycarbonyl (CBZ), 2-bromobenzyloxycarbonyl, 2-chlorobenzycarbonyl, 9-toluenesulfonyl, mesitylene-2-sulfonyl, and tert-butyloxcarconyl, t-butoxycarbonyl (BOC), or 9-fluorenylmethoxycarbonyl (Fmoc);

X is selected from the group consisting of COO-$PG_1$, wherein $PG_1$ is selected from the group consisting of benzyl, methyl, 2-adamantyl, cyclohexyl, 9-fluorenylmethyl, tert-butyl, 1-adamantyl, 4-methoxy-2,3,6-trimethyl benzensulfonyl, and 1,2,2,5,7,8-pentamethylchroman-6 sulfonyl.

Preferred embodiments of second modified (biphasic support)-template products have the structure $R^2COOH$ are shown in FIG. 2. $R^2$ is preferably selected from the group consisting of aryl, alkyl, wherein aryl is a mono- or polycyclic aromatic system comprised of 5 or 6 membered rings containing 0, 1, 2, 3, or 4 heteroatoms selected from nitrogen, oxygen and sulfur, which may be unsubstituted or substituted, wherein the substituents may be one or more groups selected from hydroxyl, halogen, cyano, trifluoromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$alkyl, or hydroxycarbonyl$C_{1-5}$alkoxy;

wherein alkyl is $C_{1-10}$alkyl, either unsubstituted or substituted, with one or more groups selected from halogen, hydroxyl, $C_{1-5}$alkycarbonylamino, aryl$C_{1-5}$alkylcarbonylamino, aryloxy, $C_{1-5}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$alkyl, $C_{1-3}$alkyl-amino, aryl$C_{0-5}$alkylaminocarbonyl, phenyl$C_{1-3}$alkylamino, aminocarbonyl$C_{0-4}$alkyl, hydroxycarbonyl $C_{0-5}$alkyl, $C_{1-8}$alkylsulfonylamino, aryl$C_{0-10}$alkylsulfonylamino, $C_{1-8}$alkyl-sufonyl, aryl$C_{0-10}$alkylsulfonyl, $C_{1-5}$alkyloxycarbonylamino, aryl$C_{1-5}$alkyloxycarbonylamino, or aryl$C_{1-5}$alkyloxy.

In some instances, two or more in the series of second reactants will be the same. However, if each of the first reactants is unique and each of the second reactants is different from the other second reactants, the number of second modified products will be the number of first reactants multiplied times the number of second reactants. Moreover, if the template contains additional functionalization sites or if one or more of the reactants contains additional functionalization sites, additional reaction steps can give rise to larger and larger combinatorial libraries.

The preferred second-modified PEG-templates is then saponified in the presence of NaOH to remove the PEG biphasic support. Preferably the NaOH concentration is 0.1M. The protecting groups on $R^1$ are also removed to yield free amines.

TABLE 2 shows generic formulas for preferred reactants having the formula $R^1NH_2$ for use in synthesizing a first-modified PEG-template.

Table 2

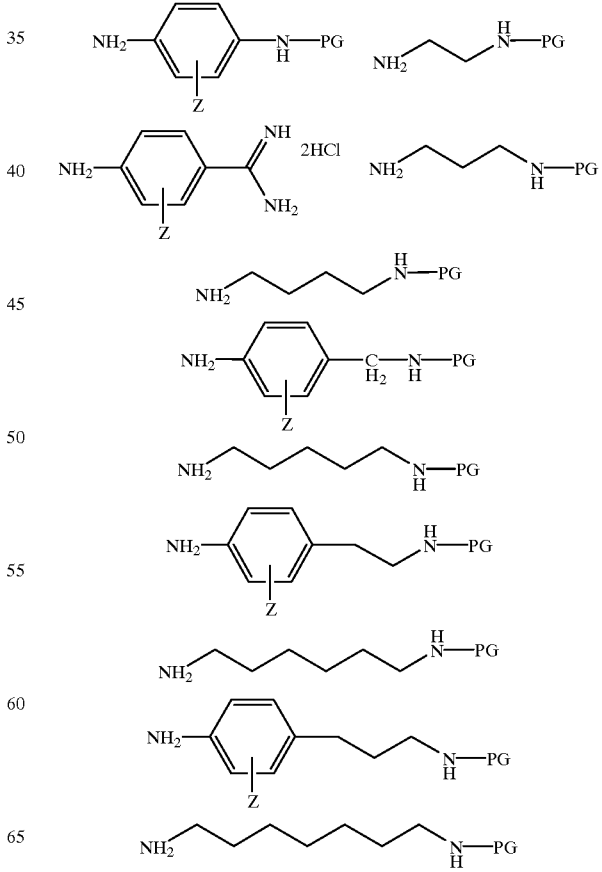

-continued

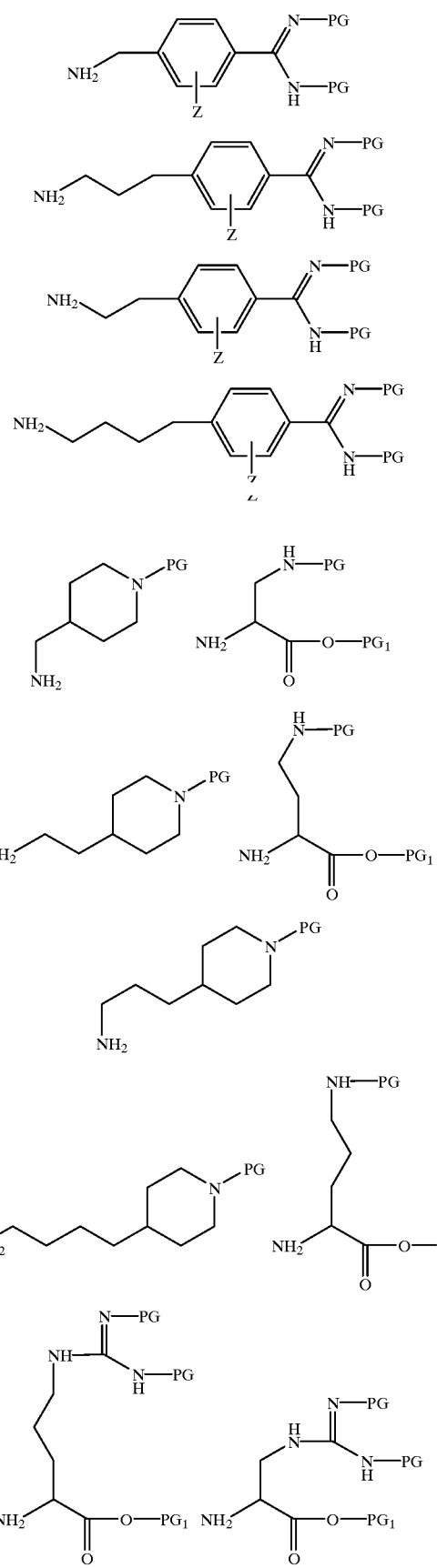

-continued

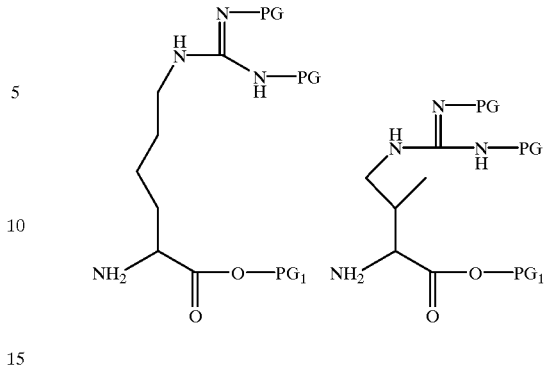

wherein Z is selected from the group consisting of hydroxyl, halogen, cyano, trifluromethyl, $C_{1-3}$alkoxy, $C_{1-5}$alkyl, $C_{1-5}$alkylcarbonyloxy, nitro, $C_{1-5}$alkoxycarbonyl, amino$C_{1-5}$alkyl.

TABLE 3 shows still more preferred $R^1NH_2$ and $R^2COOH$ reactants for use in synthesizing a chemical library. Use of these reactants generates a 3×12 combinatorial library.

In a still more preferred embodiment, the first reactants to be reacted with the (biphasic support)-template will have the formula $R^1NH_2$, and will be selected from the following compounds:

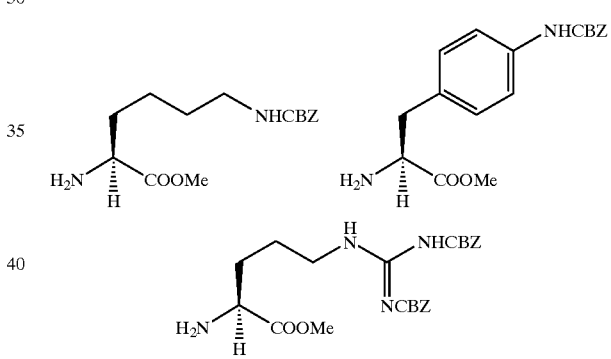

In this still more preferred embodiment, second reactants will be selected from the following group of reactants having the formula $R^2COOH$:

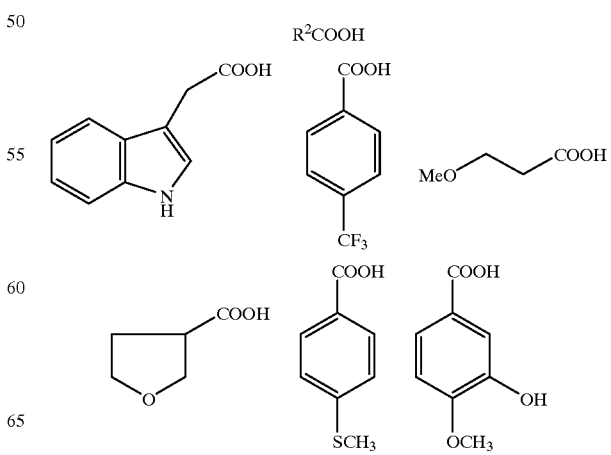

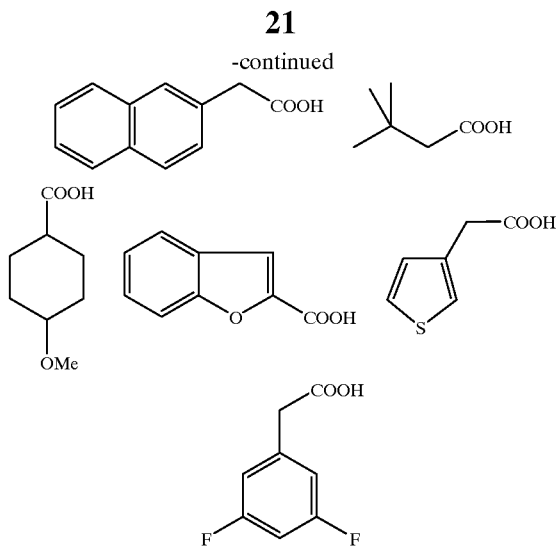

Figure 1:
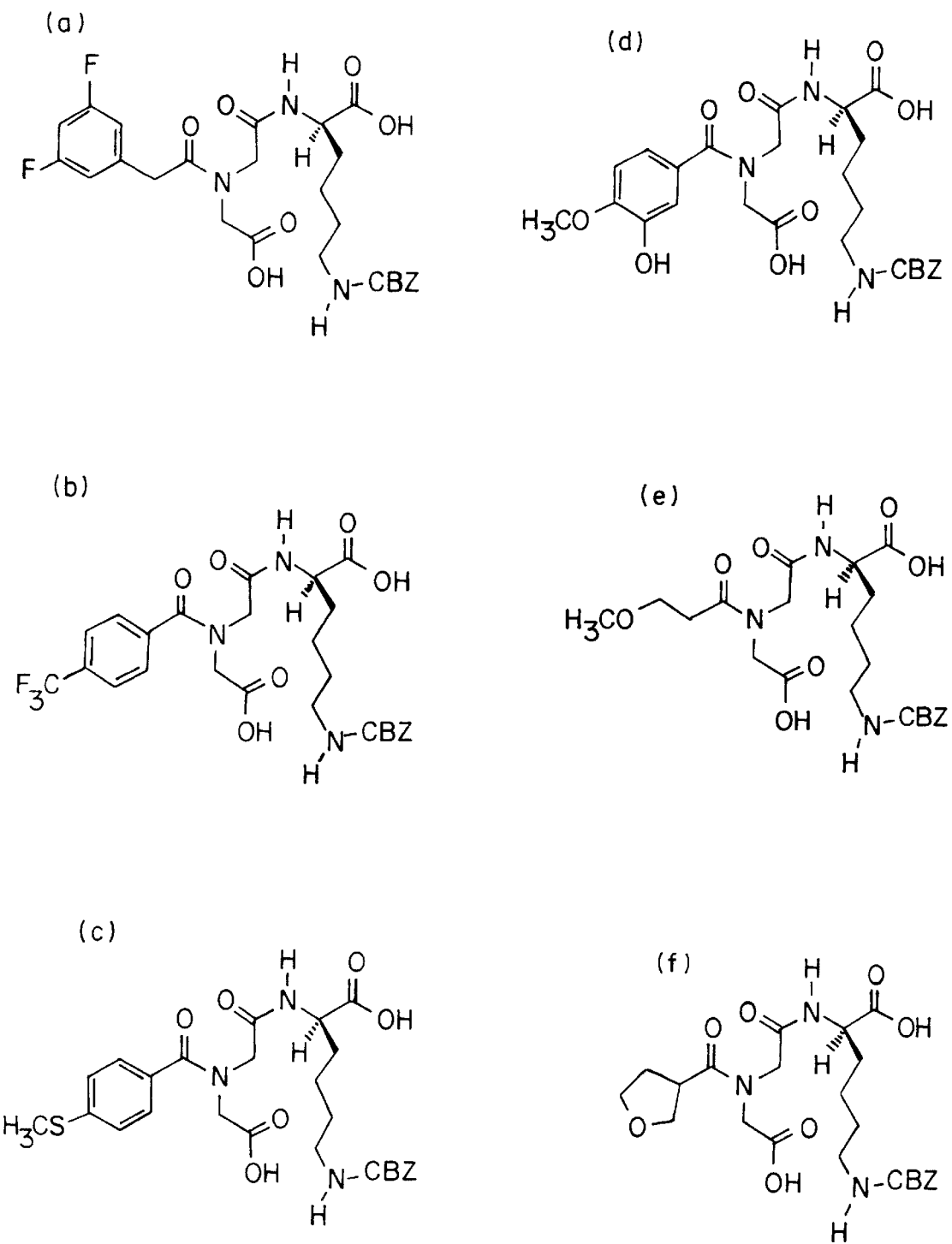
FIG. 1(a)–1(f) shows compounds in a preferred combinatorial library synthesis according to the method set forth in Scheme 1.
Figure 1:
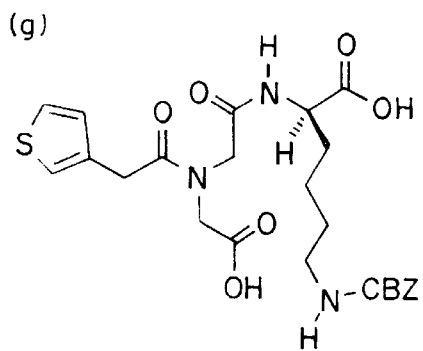
Figure 1:
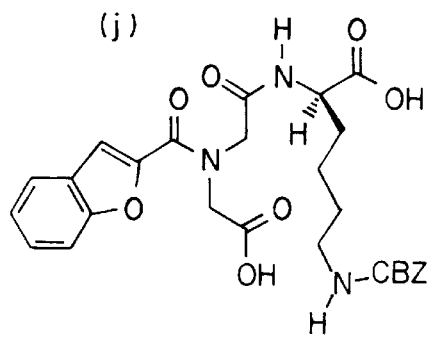
Figure 1:
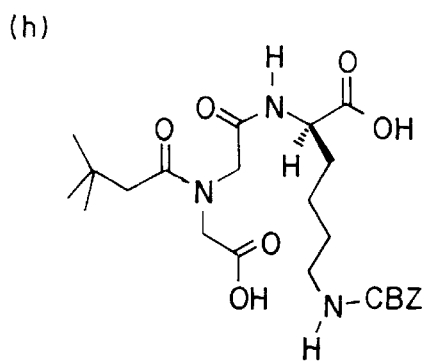
Figure 1:
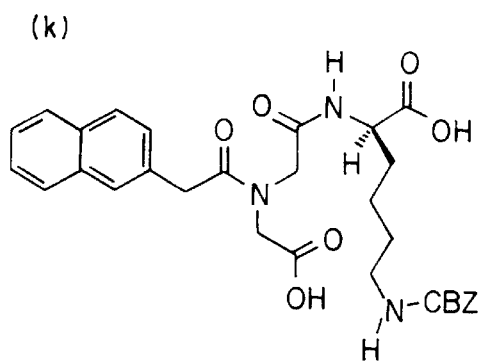
Figure 1:
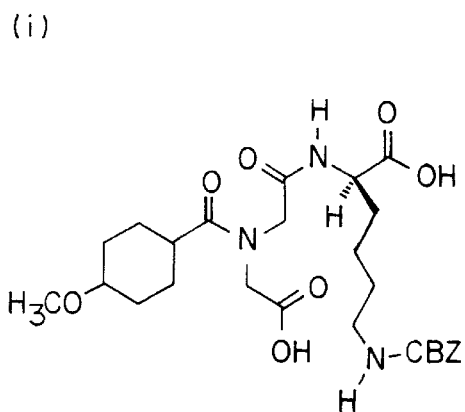
Figure 1:
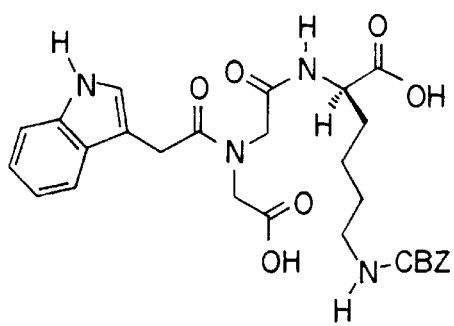
Figure 1:
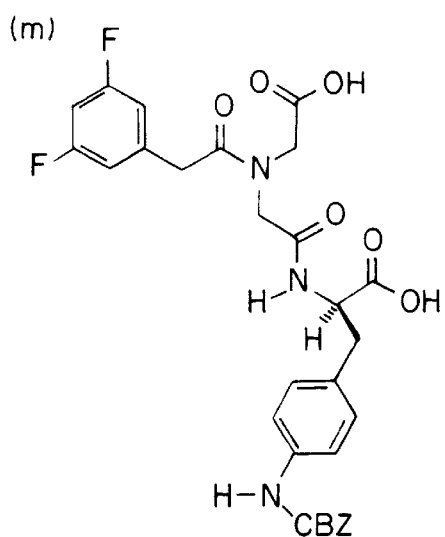
Figure 1:
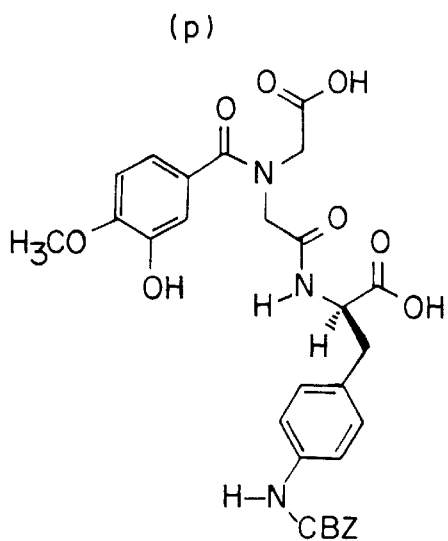
Figure 1:
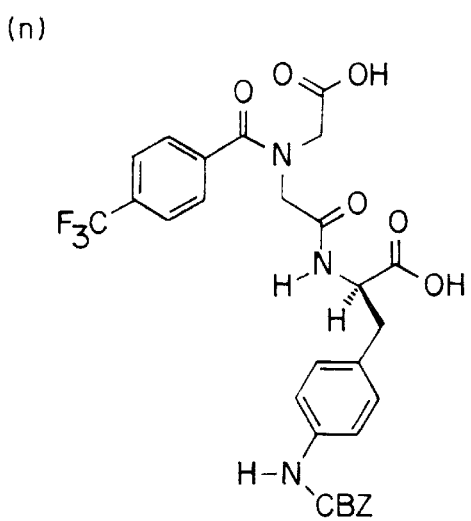
Figure 1:
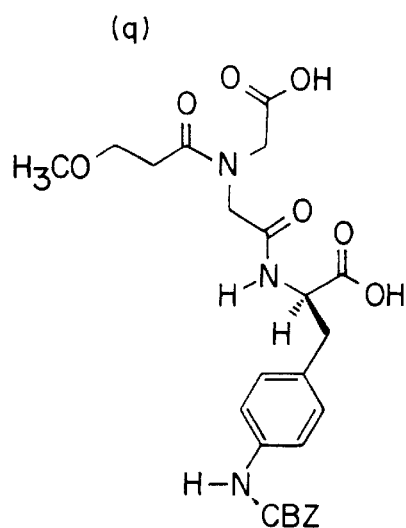
Figure 1:
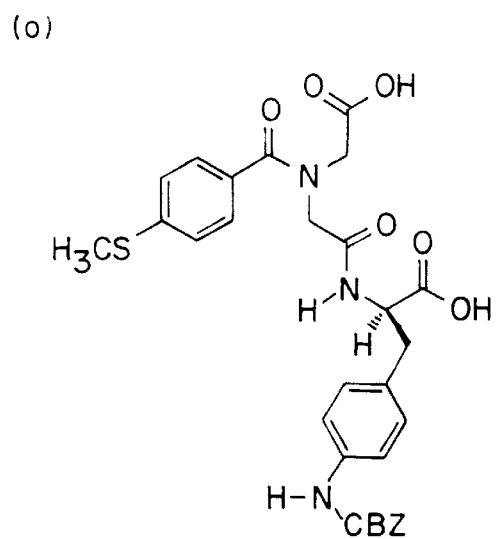
Figure 1:
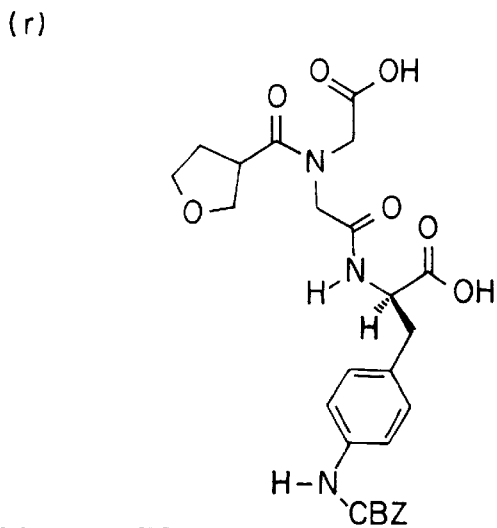
Figure 1:
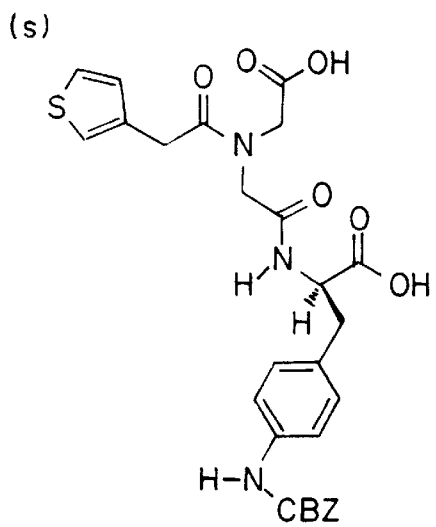
Figure 1:
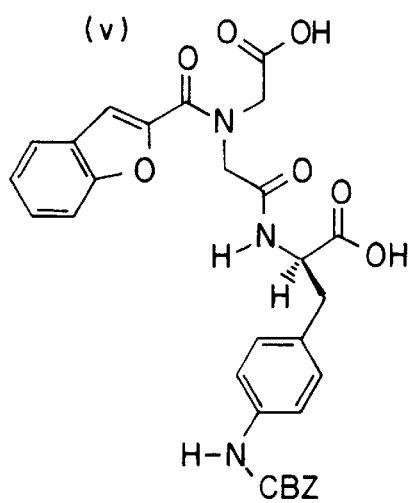
Figure 1:
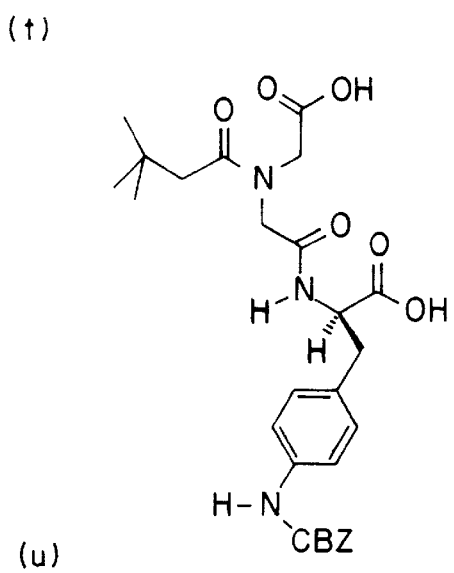
Figure 1:
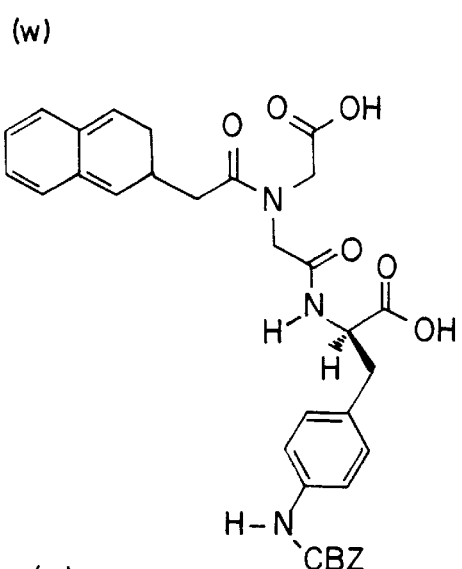
Figure 1:
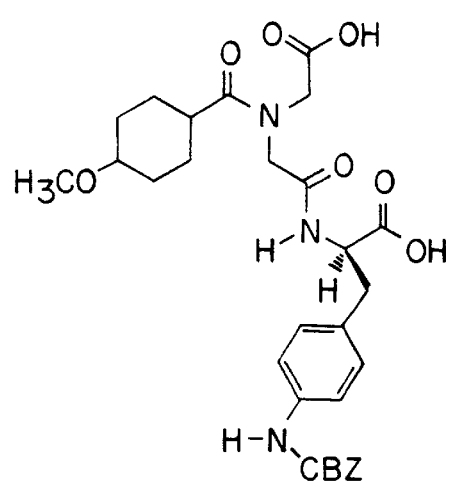
Figure 1:
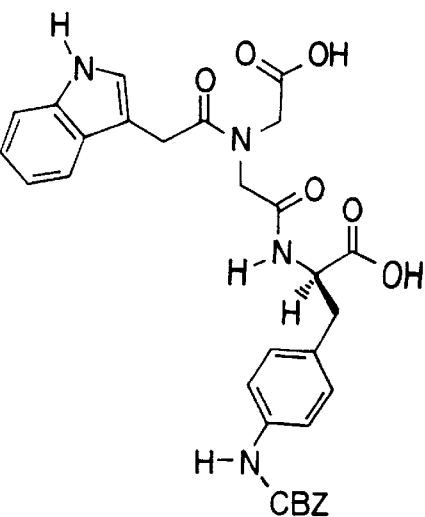
Figure 1:
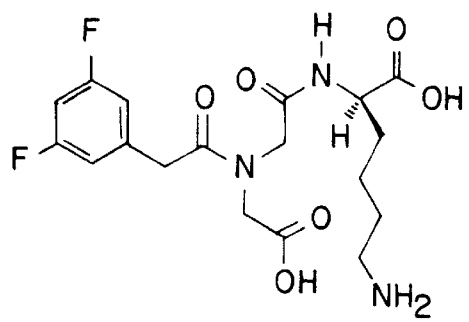
Figure 1:
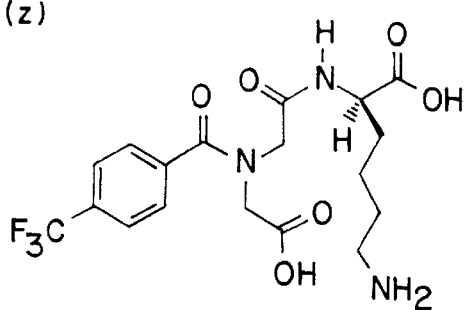
Figure 1:
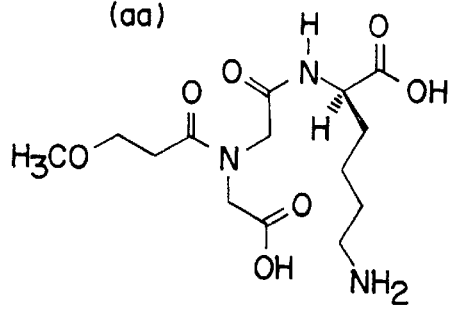
Figure 1:
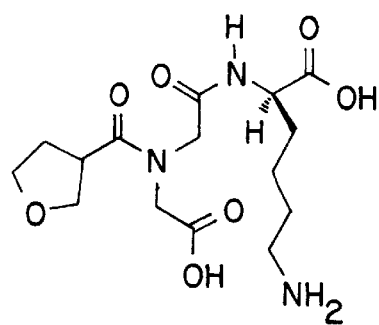
Figure 1:
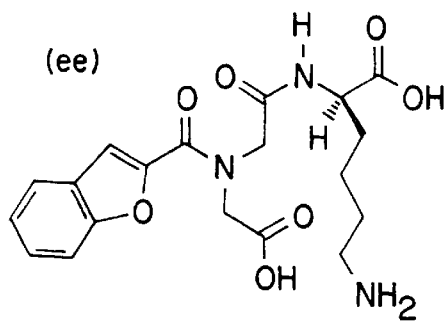
Figure 1:
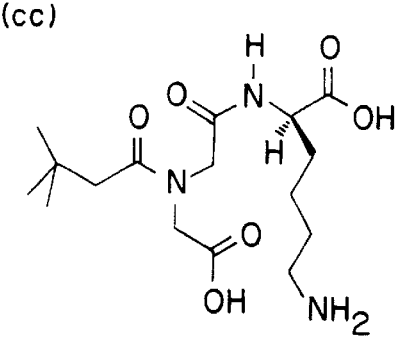
Figure 1:
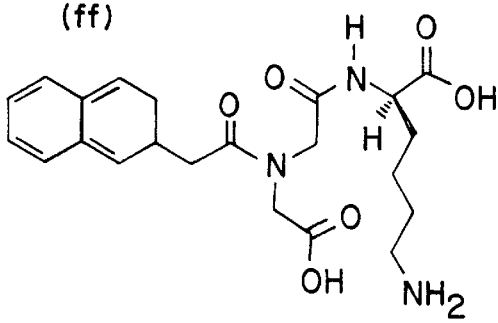
Figure 1:
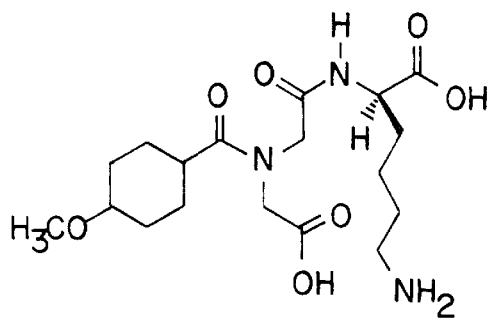

FIG. 1(a)–1(ff) shows the library of compounds synthesized using a PEG-IDA template and the reactants shown in Table 3.

In another preferred embodiment, particularly useful in the COMBISYN® matrix device, after precipitation of functionalized or modified (biphasic support)-template, the reaction mixture is transferred to a work station at which the solid phase is separated from the liquid phase. Transfer may take place, for example, by pumping the reaction mixture from the reaction vessel to the work station, or by automated or manual movement of the reaction vessel to the work station. The liquid phase containing the unreacted reactants can be removed and discarded, and the solid phase can be washed and recovered.

In a third preferred embodiment, this invention features the combinatorial library produced by the preferred method of combinatorial synthesis using a template attached to a biphasic support. Preferably, the template has two or more functionalization sites, in addition to the functionalization site at which the biphasic support will be attached. In a more preferred embodiment, the library will consist of the compounds produced by using the reactants shown in Table 2, or even more preferably, the library will consist of the compounds shown in FIG. 1(a)–1(ff).

As used herein, the term "alkyl" refers to an aliphatic hydrocarbon group or compound, preferably a saturated hydrocarbon, either unbranched or branched. The alkyl group may be optionally substituted with one or more chemical groups or functionalization sites which are attached commonly to such chains, preferably hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, and the like. The alkyl group may be cyclic or acyclic.

An alkane is a compound containing an alkyl group. As used in the preferred embodiment of $R^1NH_2$, "$C_{1-10}$alkyl" or "alkyl" refers to a straight or branched chain alkyl of 1–10 carbon atoms. As used in the preferred embodiment of $R^2COOH$, alkyl can be unsubstituted or substituted, where the substituents are one or more groups selected from halogen, hydroxyl, $C_{1-5}$alkycarbonylamino, aryl$C_{1-5}$-alkylcarbonylamino, aryloxy, alkoxy, $C_{1-5}$alkoxycarbonyl, $C_{0-5}$alkylaminocarbonyl, $C_{1-5}$alkylcarbonyloxy, $C_{3-8}$cycloalkyl, aryl, oxo, amino, $C_{1-6}$alkyl, $C_{1-3}$alkylamino, aryl$C_{0-5}$alkylaminocarbonyl, phenyl$C_{1-3}$alkylamino, aminocarbonyl$C_{0-4}$alkyl, hydroxycarbonyl $C_{0-5}$alkyl, $C_{1-8}$alkylsulfonylamino, aryl$C_{0-10}$alkylsulfonylamino, $C_{1-8}$alkylsufonyl, aryl$C_{0-10}$alkylsulfonyl, $C_{1-5}$alkyloxcarbonylamino, aryl$C_{1-5}$alkyl oxycarbonylamino, or aryl$C_{1-5}$alkoxy.

An "aryl" group is any aromatic group with a substituent group attached directly to a ring carbon. The aryl group may be substituted with one or more functionalization sites which are attached commonly to such compounds, such as hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, sulfonyl, and the like. Preferably the aromatic group in an "aryl" group in $R^1NH_2$ is phenyl or substituted phenyl.

Preferably the aryl group in $R^2COOH$, is a mono- or polycyclic aromatic system comprised of 5 or 6 membered rings containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$alkylcarbonyloxy, $C_{1-5}$alkoxycarbonyl, $C_{1-5}$alkyl, amino-$C_{1-5}$ alkyl, hydroxycarbonyl$C_{0-5}$ alkyl, or hydroxycarbonyl-$C_{1-5}$alkoxy.

A "heteroaryl" group is a 5–10 membered aromtic ring system in which one or more rings contain one or more heteroatoms selected from the group consisting of N, O or S such as, but not limited to pyrrole, pyrazole, furan, thiophene, quinoline, isoquinoline, quinazolinyl, pyridine, pyrimidine, ozazole, thiazole, thiadiazole, triazole, imidazole or benzimidazole.

A "heterocyclic" group contains a ring made up of carbon atoms and at least one other type of atom, for example, nitrogen, oxygen, or sulfur. The heterocyclic product may be aromatic or saturated, or partially unsaturated. Preferably a "heterocyclic" group is a saturated or partially unsaturated 4–10 membered ring system in which one or more rings contain one or more heteroatoms selected from the group consisting of N, O or S; such as, but not limited to, pyrrolidine, piperidine, piperazine, morpholine, tetrahydropyran or imidazolidine.

The term "alkyloxy" denotes the group -OR, where R is alkyl as defined above, such as methoxy, ethoxy, n-propoxy, iso-propoxy, n-butoxy, sec-butoxy, iso-butoxy, or tert-butoxy and the like.

A "cyclic molecule" is a molecule which has at least one chemical moiety which forms a ring. The ring may contain three atoms or more. The molecule may contain more than one cyclic moiety, the cyclic moieties may be the same or different.

An "acyclic" group does not contain a ring structure. However, the molecule may be straight or branched.

A carbon-hetero multiple bond is a multiple bond between a carbon atom and a second type of atom. Examples of carbon-hetero multiple bonds are carbon-nitrogen double bonds, carbon-nitrogen triple bonds, carbon-sulfur double bonds, or carbon-oxygen double bonds. Examples of compounds containing carbon-oxygen double bonds are carboxylic acids, ketones, aldehydes, amides, esters, and thioesters.

Preferably the synthesis will be automated. An "automated" method of synthesis is one in which a self-operating device is used to deliver at least one of the reactants to more than one reaction vessel, and to simultaneously carry out parallel multiple reactions, each in a separate reaction vessel. Each of the reactants delivered may be the same or a different reactant. The "self-operating device" is one which does not require manual manipulation for the delivery of the reactant to each reaction vessel. Delivery is the physical transfer of a reactant from a container to the reaction vessel.

Preferably the number of simultaneous reactions will be greater than 2 and less than 100. Even more preferably the number of simultaneous reactions will be eight or more reactions. In addition, two or more sets of simultaneous reactions can be carried out as part of one automated "reaction step" in a chemical synthesis of a library of compounds. The different sets of simultaneous reactions may have the same or a different starting time.

Pharmacological Compound Screening

The combinatorial libraries of the present invention may be screened for pharmacologically active compounds. Combinatorial library compounds that bind to individual cellular receptors, or functional portions of the individual cellular receptor (and may additionally be capable of disrupting receptor function) may be identified.

One such method for identifying an agent to be tested for an ability to bind to and potentially modulate a cellular receptor signal transduction pathway is as follows. The method involves exposing at least one compound from the combinatorial libraries of the present invention to a protein comprising a functional portion of a cellular receptor for a time sufficient to allow binding of the combinatorial library compound to the functional portion of the cellular receptor; removing non-bound compound; and determining the presence of the compound bound to the functional portion of the cellular receptor, thereby identifying a compound to be tested for an ability to modulate a cellular receptor signal transduction pathway.

One method utilizing this approach that may be pursued in the isolation of such receptor-binding molecules would include the attachment of a combinatorial library molecule, or a portion thereof, to a solid matrix, such as agarose or plastic beads, microtiter wells, petri dishes, or membranes composed of, for example, nylon or nitrocellulose, and the subsequent incubation of the attached combinatorial library molecule in the presence of a potential combinatorial library molecule-binding compound or compounds. Attachment to said solid support may be direct or by means of a combinatorial-library-compound-specific antibody bound directly to the solid support. After incubation, unbound compounds are washed away, component-bound compounds are recovered. By utilizing this procedure, large numbers of types of molecules may be simultaneously screened for receptor-binding activity.

Pharmaceutical Administration

When used as a therapeutic the compounds isolated from the combinatorial library of the present invention are preferably administered with a physiologically acceptable carrier.

Compounds acting as antagonists of the RGD motif may be useful in treating a number of diseases associated with abnormal ECM function, such as cardiovascular disease, cancer, osteoporosis, and inflammation. In addition, the RGD peptide is small enough to encourage the development of analogs including small nonpeptide molecules. Binding between an RGD sequence on the thrombogenic surface with a receptor on the platelet cells is a final step in platelet aggregation. Thus, inhibition of the binding of fibrinogen to the $\alpha\pi b\beta 3$ complex on activated platelets by molecules having structures based on the RGD tripeptide sequence is a promising approach for the inhibition of platelet aggregation and subsequent thrombus formation because it targets the final step in the aggregation process. To be clinically useful as an antithrombotic therapeutic, glycoprotein $\alpha\pi\beta 3$ inhibitors must not causing unwanted bleeding or hemorrhagic complications at doses providing effective inhibition of platelet aggregation. RGD analogs synthesized according to the methods of this invention will be useful in treating diseases and conditions involving abnormal cell attachment, such as cardiovascular disease, cancer, osteoporosis, and inflammation.

In addition, analogs of the ELR are also likely to have therapeutic effects because the ELR sequence occurs close to the N-terminus in all C-X-C chemokine that demonstrate biological activation of neutrophils, it suggests that the ELR motif is essential for receptor binding, even though it is not the sole determinant for binding. Molecules which compete for the ELR binding site to the C-X-C chemokine receptor should antagonize the binding of the endogenous ligand and hence prove to be useful in the treatment of C-X-C chemokine driven diseases such as rheumatoid arthritis, asthma, and acute respiratory distress syndrome (ARDS).

The compounds can be prepared as pharmaceutically acceptable salts (i.e., non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See, e.g., supra. PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluene-sulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipient can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. The compounds or pharmaceutical composition can be administered by different routes including intravenously, intraperitoneally, subcutaneously, and intramuscularly; orally, topically, or transmucosally.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, many small organic molecules may be directly administered intracellularly.

Pharmaceutical compositions suitable for use in the present invention include compositions wherein the active ingredients are contained in an effective amount to achieve its intended purpose. Determination of the effective amounts is within the capability of those skilled in the art, especially in light of the detailed disclosure provided herein.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For any compound used in the method of the invention, the therapeutically effective does can be estimated initially from cell culture and animal models. For example, a dose can be formulated in animal models to achieve a circulating concentration range that includes the $IC_{50}$ as determined in cell culture. Such information can be used to more accurately determine useful doses in humans.

A preferred physiological carrier is PBTE:D5W. PBTE consists of a solution of 3% w/v benzyl alcohol, 8% w/v polysorbate 80, and 65% w/v polyethylene glycol (MW=300 daltons) in absolute ethanol. PBTE:D5W consists of PBTE diluted 1:1 in a solution of 5% dextrose in water.

The use of hydrophobic compounds can be facilitated by different techniques such as combining the compound with a carrier to increase the solubility of the compound and using frequent small daily doses rather than a few large daily doses. For example, the composition can be administered at short time intervals, such as by the methods described above or using a pump to control the time interval or achieve continuous administration. Suitable pumps are commercially available (e.g., the ALZET® pump sold by Alza corporation, and the BARD ambulatory PCA pump sold by Bard MedSystems).

The proper dosage depends on various factors such as the type of disease being treated, the particular composition being used, and the size and physiological condition of the patient. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/day, most preferably 0.2 to 15 mg/kg/day. Alternatively, drugs can be administered at 0.5 to 1200 mg/m²/day, preferably 0.5 to 150 mg/m²/day, most preferably 5 to 100 mg/m²/day. The average plasma level should be 50 to 5000 µg/ml, preferably 50 to 1000 µg/ml, and most preferably 100 to 500 µg/ml. Plasma levels may be reduced if pharmacological effective concentrations of the drug are achieved at the site of interest.

EXAMPLES

Herein, we detail a high-speed synthesis of two chemical libraries containing small organic molecules using PEG resin as a soluble support.

The use of PEG resin as a soluble support for the synthesis of small organic molecules is demonstrated by the synthesis of two chemical libraries. One library was designed that features pharmacophores attached to the iminodiacetic acid template. This library was synthesized on PEG resin using a four-steps reaction sequence. In each step of the sequence, the excess reagents and their byproducts are removed by simple filtration providing the desired final compounds in high purities without chromatography. The versatility of this strategy is illustrated by the synthesis of a chemical library containing small-ring heterocycles.

Example 1

Attachment of a iminodiacetic acid template to PEG

Synthesis of a library of multifunctionalized templates was carried out according to Scheme 1. BOC-iminodiacetic acid (4.66 g, 20.0 mmol) and dicyclohexylcarbodiimide (DCC) (4.12 g, 20.0 mmol) were stirred together in dichloromethane (DCM) (25 ml) for 1 hr. at room temperature. Precipitated dicyclohexyl urea was removed by gravity filtration and the clear mother liquor was combined with a solution of 15 g of polyethylene glycol (PEG) monomethyl ether (M.W.=5,000) and pyridine (6.25 ml) in DCM (100 ML). The resulting solution was concentrated to a volume of about 75 ml and the mixture stirred overnight at room temperature. After stirring overnight, diethyl ether (400 ml) was added slowly to the solution while cooling in an ice bath to 0° C. The PEG-bound product precipitated out and was collected on a filter and washed with diethyl ether (3×30 ml). The white powder was redissolved in dry EtOH (300 ml) at 40° C. and allowed to recrystallize overnight. After recrystallization overnight, the product was collected on a filter and washed with diethyl ether (200 ml). The white solid PEG bound product (2) was dried overnight in vacuo (14.8 g, 98% recovery). The reaction products were confirmed by proton NMR.

Example 2

Synthesis of Monofunctionalized PEG-templates (Structure 2, 12.0 g, 2.4 mmol) and Lys(CBZ)-OMe (5.4 mmol, 2.25 eq) were stirred together in DCM/DMF 36/64 ml until the solids dissolved. Diisopropylethylamine (DIEA) (3.7 ml, 21.6 mmol, 9.0 eq.) was added followed by PyBOP (3.822 g, 7.2 mmol, 3.0 eq.). The mixture was stirred overnight at room temperature. The monofunctionalized PEG-template products was precipitated by adding diethyl ether (300 ml) to the stirred solution. The white solid was collected on a filter and washed with diethyl ether (3×30 ml). The PEG bound product (3) was then recrystallized from warm EtOH (250 ml, 40° C.), collected on a filter, washed with diethyl ether (3×30 ml), and dried overnight in vacuo (11.5 g, 95% recovery). The products were confirmed by proton NMR.

Example 3

Synthesis of a DiFunctionalized PEG-Template

Structure 3 (11.0 g, 2.2 mmol) was treated with TFA/DCM 1:1 (75 ml). The resulting clear solution was stirred at room temperature for 30 min. Most of the solvent and TFA was removed in vacuo and then diethyl ether (300 ml) was added to precipitate out the PEG bound TFA salt product. The product was collected on a filter and washed 4×50 ml diethyl ether and air dried. The white solid was then recrystallized from warm EtOH (220 ml) at 40° C. and collected on a filter and washed with diethyl ether (6×50 ml). The PEG bound TFA salt product was dried overnight in vacuo (9.45 g). The whole 9.45 g was then dissolved in DCM/DMF 20/52 ml and DIEA (3.44 ml, 9.0 eq.) was added and mixed. Twelve 7 ml portions were removed and each put into a vial containing one of the carboxylic acids listed in $R^2COOH$ in Table 2 (4.0 eq.) PyBOP (0.380 g, 4.0 eq.) was then added to each vial. The mixtures were stirred overnight at room temperature and were precipitated out with diethyl ether (100 ml each) the next day. Each precipitate was collected separately on a filter and washed 4×10 ml diethyl ether. Each solid was recrystallized from dry EtOH (15 ml) and collected separately on a filter and washed 4×10 ml diethyl ether. Difunctionalized PEG-template products having the structure shown in (4) were dried overnight in vacuo. Average recovery=66%.

Example 4

General Procedure for the Cleavage of PEG from the Difunctionalized PEG-Templates By Saponification with NaOH Each of the PEG bound products generated from compounds having the Structure shown in structure (4) was treated with a solution of 0.1M NaOH/Dioxane 1:1 (3 ml). The resulting clear solutions were stirred for 90 min. at room temperature. Each mixture was then acidified to pH 2–3 with 10% HCl (10 ml) and extracted 2× EtOAc (25 ml). EtOAc washes were combined and washed with brine (1×25 ml). The organic solutions were then dried over $Na_2SO_4$, filtered, and evaporated to dryness. The products having structure (5) were dried overnight in vacuo. (average yield=52%, 11/12 products 97% pure by LC/MS).

Example 5

Attachment of GLY to PEG

BOC-GLY-OH (5.6 g. 32 mmol) was dissolved in methylene chloride (40 ml) and dicyclohexylcarbodiimide (DCC) (3.30 g, 16 mmol) was added. The reaction mixture was stirred at room temperature for 30 minutes and the resulting precipitate of DCU was filtered off. The clear solution was added to polyethylene glycol monomethyl ether (M.W=5,000) solution (12 g in 80 ml of methylene chloride). Pyridine (5 ml) was added to the reaction mixture and the solution was concentrated in vacuo to about 50 ml. The reaction mixture was stirred at room temperature overnight. The product was precipitated by adding diethyl ether to the stirred solution. The mixture was stirred at 0° C. for 15 min. and filtered. The product was washed several times with ether and dried in vacuo.

Example 6

Synthesis of Thiazolidinone

PEG-bound GLY (2 g, 0.4 mmol) was dissolved in a mixture of $CH_2$/TFA (1:1, 16 ml) and was stirred at room temperature for 30 minutes.

The solvent was concentrated in vacuo to about 8 ml. The product was precipitated by adding diethyl ether to the stirred solution. The mixture was stirred at 0° C. for 15 min. and filtered. The product was washed several times with ether and dried in vacuo. The N-deprotected product was dissolved in benzene (8 ml) and was treated with DIEA (78 mg, 105 ml, 0.6 mmol) followed by CHO (480 mg, 4.0 mmol), (736 mg, 8.0 mmol) and molecular sieves (60 pellets). The mixture was heated at 70° C. for 2 h. The product was precipitated by adding diethyl ether to the stirred solution. The crude product was recrystalized from ethanol/ether solution.

Example 7

Hydrazinolysis

PEG-bound thiazolidinone (264 mg) was dissolved in methanol (4 ml) and hydrazine hydrate (400 ml) was added. The solution was stirred at room temperature overnight and evaporated to dryness. The residue was dissolved in methanol (10 ml), evaporated to dryness and redissolved in methanol (3 ml). PEG was precipitated by adding ether. The mixture was left at 0° C. for 20 min. and filtered. The filtrate containing the cleared hydrazide was evaporated to dryness.

The following scheme shows examples of generic thiazolidinones which can be prepared using this method.

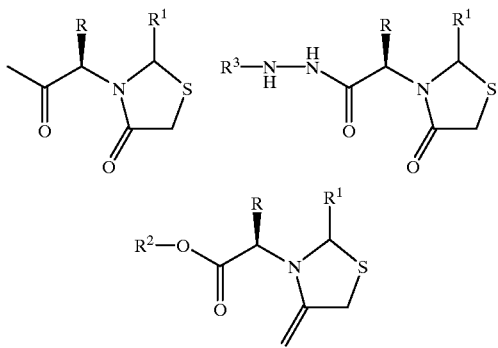

R,R$^1$,R$^2$,R$^3$ alkyl, aryl, heteroaryl, heterocyclic, hydrogen

All patents and publications mentioned in this specification are indicative of the levels of those skilled in the art to which the invention pertains. All patents and publications are herein incorporated by reference to the same extent as if each individual publication is specifically and individually indicated to be incorporated by reference.

Other embodiments are within the following claims. Thus while several embodiments have been shown and described, various modifications may be made to the invention disclosed herein, without departing from the spirit and scope of the present invention.

Example 8

Receptor and Ligand Purifications

Receptors will be purified according to published procedures (Pytela, R.; Pierschbacher, M. D.; Argraves, W. S.; Suzuki, S.; Ruoslahti, E. Arginine-Glycine-Aspartic Acid Adhesion Receptors. Methods Enzymol. 1987, 144, 475–489) with some modifications. Briefly, vitronectin receptor ($\alpha_v\beta_5$) will be purified by RGD peptide-affinity chromatography from 100 mM octyl glucoside (OG)-extracted human placenta. After extraction, the suspension will be adsorbed to a Sepharose CL4B column and then applied to a GRGDSPK affinity column. Except where stated, all procedures will be carried out at 4° C. The peptide column will be washed with five volumes of Tris-buffered saline (TBS) containing 3 mM Ca$^{2+}$ and 50 mM OG and then with five column volumes of TBS containing 3 mM Ca$^{2+}$ and 50 mM OG at room temperature. Elution of bound receptor will be carried out at room temperature with TBS containing 10 mM EDTA and 50 mM OG. Finally, 12 mM Ca$^{2+}$ will be added to eluted fractions.

Fibronectin receptor ($\alpha_5\beta_1$) can be similarly purified from 100 mM OG-extracted human placenta using a procedure identical to that for the $\alpha_v\beta_5$ up to and including the initial Sepharose chromatography step. However, following this step, the Sepharose CL4B column flow-through will be brought to 3 mM Mn$^{2+}$ and the resulting solution run over a 110 kDa fibronectin fragment-affinity column. Washing and elution steps will be carried out the same as those used in purifying vitronectin receptor, with the exception of the use of MnCl$_2$ rather than CaCl$_2$ in the wash buffer.

Platelet glycoprotein $\alpha_{IIb}\beta_3$ will be purified from outdated human platelets. Briefly, the platelets will be centrifuged for 10 min at 800 g to pellet RBC's. The platelets will then be washed three times with 20 mM Tris-HCl, 150 mM NaCl (TBS), 1 mM EDTA, 0.2% glucose, pH 7.5, and centrifuged at 1500 g to pellet cells. Cells will be lysed in two pellet volumes of TBS, 100 mM OG, 1 mM MnCl$_2$, 1 mM MgCl$_2$, and 0.1 mM PMSF, followed by centrifugation at 30000 g. The supernatant fraction will be collected and loaded onto a Sepharose 2B column, previously equilibrated in TBS, 1 mM MnCl$_2$, 1 mM MgCl$_2$, and 0.1 mM PMSF, 100 mM OG. Flow-through from the Sepharose 2B column will be collected and passed over a GRGDSPK-Sepharose affinity column. The column will be eluted with TBS containing 50 mM OG and 1 mg mL GRGDSP. The fractions, after collecting and pooling, will be diafiltered and concentrated on an Amicon YM 30 filter.

Human fibrinogen can be purchased from Calbiochem.

Example 9

$\alpha_5\beta_1$ ELISA Assay

Peptide binding to purified $\alpha_5\beta_1$ will be determined by using a competitive enzyme-linked immunosorbent assay (ELISA) in which fibronectin is immobilized and the binding of solubilized $\alpha_5\beta_1$, in the presence of various concentrations of a peptide analogue, is detected with a polyclonal anti-FnR antibody followed by a labelled anti-rabbit IgG conjugate.

Microtiter plates will be coated overnight at room temperature with 110 µL of human fibronectin (at 2 µg/mL) in TBS. The plates will be washed three times with TBS that contained 0.05% Tween-20. $\alpha_5\beta_1$ receptor in TBS containing 20 mM octyl glucoside and 2 mM MnCl$_2$ will be added to each well. Next, 50 µL of peptide in the same buffer will be added in 10-fold serial dilutions. The plates will be incubated for 3 h at room temperature and washed with 200 µL of the above TBS-Tween buffer. Bound receptor can be detected by incubation with 100 µL of affinity-purified rabbit anti-human fibronectin receptor antibody for 2 h, washed twice with TBS-Tween and then distilled water. Affinity-purified goat anti-rabbit IgG conjugated to horseradish peroxidase (100 µL) can then be added to each well and incubated overnight at room temperature. The following day, the plates will be washed with TBS-Tween and then distilled water. Then, 100 µL of substrate mixture (10 mg of o-phenylenediamine in 25 mL of 0.1M citrate-phosphate buffer, pH 5.0, plus 6 µL of 30% H$_2$O$_2$) will be added to the plates and be allowed to develop in the dark. The development process will be stopped by adding 50 µL of 4 NH$_2$SO$_4$ to each well.

Example 10

$\alpha_{IIb}\beta_3$ ELISA

Peptide binding to purified $\alpha_{IIb}\beta_3$ will be determined in a similar ELISA system. The steps will be the same as described above except the microtiter plates will be coated with human fibrinogen at 10 µg/mL diluted in TBS, purified $\alpha_{IIb}\beta_3$ will be diluted in TBS with 20 mM octyl glucoside containing 2 mM MgCl$_2$ and 2 mM CaCl$_2$, and rabbit anti-$\alpha_{IIb}\beta_3$ will be used to detect bound receptor.

Example 11

$\alpha_v\beta_5$ ELISA

Peptide binding to purified $\alpha_v\beta_5$ will be determined in a similar ELISA. The steps will be identical with the $\alpha_5\beta_1$ ELISA except that microtiter plates were coated with purified human vitronectin diluted to 10 mg/mL in 0.1M carbonate buffer (pH 9.6), purified human $\alpha_v\beta_5$ will be diluted in TBS containing 20 mM octyl glucoside, 2 mM MgCl$_2$, and 2 mM CaCl$_2$, and affinity purified rabbit anti-VnR was used to detect bound receptor.

Example 12

Platelet Aggregation Assay

Ex vivo platelet aggregation will be determined by established spectrophotometric methods with a four-channel aggregometer (BioData-PAP-4, BioData Corporation, Hatboro, Pa.) by recording the increase in light transmission through a stirred suspension of PRP maintained at 37° C. Aggregation will be induced with ADP (10 $\mu$M) or collagen (10 $\mu$g/mL). Values will be expressed as a percentage of aggregation. This represents the percentage of light transmission standardized to PRP and PPP samples yielding 0% and 100% light transmission, respectively.

Blood (20 mL) will be withdrawn from the cephalic vein into a plastic syringe containing 3.2% sodium citrate. The platelet count will be determined with a Haema count MK-4/HC system (J. T. Baker, Allentown, Pa.). Platelet-rich plasma (PRP), the supernatant present after centrifuging anticoagulated whole blood at 1000 rpm for 5 min (140 g), will be diluted with platelet-poor plasma PPP) to achieve a platelet count of 200 000/$\mu$L. PPP will be prepared after the PRP is removed by centrifuging the remaining blood at 12000 g for 10 min and discarding the bottom cellular layer.

All aggregation studies will be performed at 37° C. with a constantly stirred suspension of 2×10$^8$ platelets/mL. Peptides and stimulants will be added to these suspensions in 1% dilutions. The PRP and gel-filtered platelets will be used within 3 h from the time of blood collection.

Peptide anti-aggregation potencies will be determined from dose-response curves for the inhibition of the maximum aggregation responses stimulated by physiologic doses of ADP (10 $\mu$M) and thrombin (2 U/mL). The 50% inhibitory concentration of each peptide (IC$_{50}$) will be determined by regression analysis of these curves. Individual data points are accurate to ±15%.

Assays for ELR agonist or antagonist activity of peptides will be carried out in a similar fashion to the above assays, except that the neutrophil receptor for the ELR peptide of a compound will be used in peptide binding studies. The ability to inhibit neutrophil activation can also be used to assay biological activity of members of the chemical library.

TABLE 3

Molecular weights of compounds shown in FIG. 1

| Compound | M + 1 value from LCMS |
| --- | --- |
| 1 (a) | 550.2 |
| 1 (b) | 568.2 |
| 1 (c) | 546.4 |
| 1 (d) | 546.2 |
| 1 (e) | 482.0 |
| 1 (f) | 494.2 |
| 1 (g) | 520.4 |
| 1 (h) | 494.2 |
| 1 (i) | 536.2 |
| 1 (j) | 540.2 |
| 1 (k) | 564.2 |
| 1 (l) | 553.2 |
| 1 (m) | 584.2 |
| 1 (n) | 602.4 |
| 1 (o) | 580.2 |
| 1 (p) | 472.2 |
| 1 (q) | 516.4 |
| 1 (r) | 528.4 |
| 1 (s) | 554.2 |
| 1 (t) | 528.4 |
| 1 (u) | 570.4 |
| 1 (v) | 574.4 |

TABLE 3-continued

Molecular weights of compounds shown in FIG. 1

| Compound | M + 1 value from LCMS |
| --- | --- |
| 1 (w) | 598.4 |
| 1 (x) | 587.4 |
| 1 (y) | 416.2 |
| 1 (z) | 434.2 |
| 1 (aa) | 348.1 |
| 1 (bb) | 360.2 |
| 1 (cc) | 360.2 |
| 1 (dd) | 416.2 |
| 1 (ee) | 406.2 |
| 1 (ff) | 564.4 |

What is claimed is:

1. A combinatorial library comprising a collection of compounds having the formula

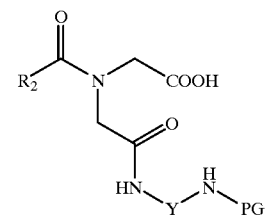

wherein R$_2$ is selected from the group consisting of aryl, alkyl, wherein aryl is a mono- or polycyclic aromatic system comprised of 5 or 6 membered rings containing 0, 1, 2, 3, or 4 heteroatoms selected from nitrogen, oxygen and sulfir, which may be unsubstituted or substituted, wherein the substituents may be one or more groups selected from hydroxyl, halogen, cyano, trifluoromethyl, C$_{1-3}$alkoxy, C$_{1-5}$alkylcarbonyloxy, C$_{1-5}$alkoxycarbonyl, C$_{1-5}$alkyl, aminoC$_{1-5}$alkyl, hydroxycarbonylC$_{0-5}$alkyl, or hydroxycarbonyl C$_{1-5}$alkoxy;

and wherein alkyl is C$_{1-10}$alkyl, either unsubstituted or substituted, with one or more groups selected from halogen, hydroxyl, C$_{1-5}$alkylcarbonylamino, arylC$_{1-5}$alkylcarbonylamino, aryloxy, C$_{1-5}$alkoxy, C$_{1-5}$alkoxycarbonyl, C$_{0-5}$alkylaminocarbonyl, C$_{1-5}$alkylcarbonyloxy, C$_{3-8}$cycloalkyl, aryl, oxo, amino, C$_{1-6}$alkyl, C$_{1-3}$alkylamino, arylC$_{0-5}$alkylaminocarbonyl, phenylC$_{1-3}$alkylamino, aminocarbonylC$_{0-4}$alkyl, hydroxycarbonyl C$_{0-5}$alkyl, C$_{1-8}$alkylsulfonylamino, arylC$_{0-10}$alkylsulfonylamino, C$_{1-8}$alkylsulfonyl, arylC$_{0-10}$alkylsulfonyl, C$_{1-5}$alkyloxycarbonylamino, arylC$_{1-5}$alkyl-oxycarbonylamino or arylC$_{1-5}$alkyloxy;

and wherein -Y- is selected from the group consisting of

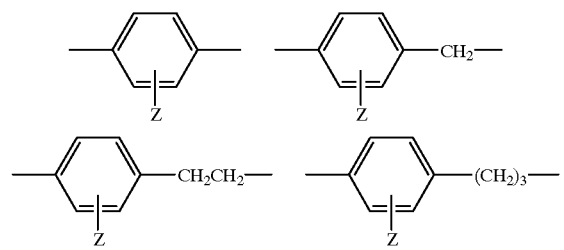

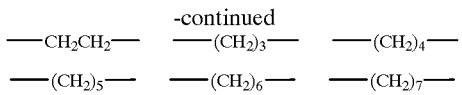

and wherein Z is selected from the group consisting of hydroxyl, halogen, cyano, trifluoromethyl, $C_{1-3}$alkoxy, $C_{1-5}$alkyl, $C_{1-5}$alkylcarbonyloxy, nitro, $C_{1-5}$alkoxycarbonyl, and amino$C_{1-5}$alkyl;

and wherein PG is selected from the group consisting of benzyloxycarbonyl, 2-bromobenzyloxycarbonyl, 2-chlorobenzycarbonyl, 9-toluenesulfonyl, mesitylene-2-sulfonyl, and tert-butoxycarbonyl or 9-fluorenylmethoxycarbonyl.

2. A combinatorial library comprising a collection of compounds having the formula

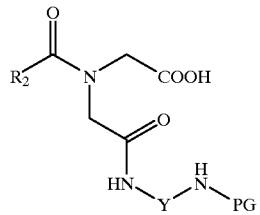

wherein $R_2$ is selected from the group consisting of aryl, alkyl, wherein aryl is a mono- or polycyclic aromatic system comprised of 5 or 6 membered rings containing 0, 1, 2, 3, or 4 heteroatoms selected from nitrogen, oxygen and sulfur, which may be unsubstituted or substituted, wherein the substituents may be one or more groups selected from hydroxyl, halogen, cyano, trifluoromethyl, $C_{1-3}$alkoxy, $C_{1-5}$alkylcarbonyloxy, $C_{1-5}$alkoxycarbonyl, $C_{1-5}$alkyl, amino$C_{1-5}$alkyl, hydroxycarbonyl$C_{0-5}$alkyl, or hydroxycarbonyl$C_{1-5}$alkoxy;

and wherein alkyl is $C_{1-10}$alkyl, either unsubstituted or substituted, with one or more groups selected from halogen, hydroxyl, $C_{1-5}$alkylcarbonylamino, aryl$C_{0-5}$alkylcarbonylamino, aryloxy, $C_{1-5}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$alkyl, $C_{1-3}$alkylamino, aryl$C_{0-5}$alkylaminocarbonyl, phenyl$C_{1-3}$akylamino, aminocarbonyl$C_{0-4}$alkyl, hydroxycarbonyl $C_{0-5}$alkyl, $C_{1-8}$alkylsulfonylamio, aryl$C_{1-10}$alkylsulfonylamino, $C_{1-8}$alkylsulfonyl, aryl$C_{0-10}$alkylsulfonyl, $C_{1-5}$alkyloxycarbonylamino, aryl$C_{1-5}$alkyloxycarbonylamino or aryl$C_{1-5}$alkyloxy;

and wherein -Y- is selected from the group consisting of cycloalkyl,

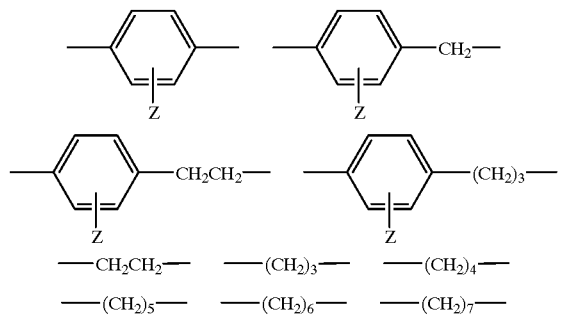

and wherein Z is selected from the group consisting of hydroxyl, halogen, cyano, trifluoromethyl, $C_{1-3}$alkoxy, $C_{1-5}$alkyl, $C_{1-5}$alkylcarbonyloxy, nitro, $C_{1-5}$alkoxycarbonyl, and amino$C_{1-5}$alkyl;

and wherein PG is selected from the group consisting of benzyloxycarbonyl, 2-bromobenzyloxycarbonyl, 2-chlorobenzycarbonyl, 9-toluenesulfonyl, mesitylene-2-sulfonyl, and tert-butoxycarbonyl or 9-fluorenyhnethoxycarbonyl.

* * * * *